US007883895B2

(12) United States Patent
Yamazaki

(10) Patent No.: US 7,883,895 B2
(45) Date of Patent: Feb. 8, 2011

(54) METHODS FOR ENHANCED BACTERIAL EXOPOLYSACCHARIDE PRODUCTION

(75) Inventor: Motohide Yamazaki, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/633,669

(22) Filed: Dec. 8, 2009

(65) Prior Publication Data
US 2010/0093095 A1 Apr. 15, 2010

Related U.S. Application Data

(62) Division of application No. 10/897,981, filed on Jul. 23, 2004, now Pat. No. 7,645,600.

(51) Int. Cl.
C12N 15/74 (2006.01)
C12N 9/00 (2006.01)
C12N 1/20 (2006.01)
C12N 15/00 (2006.01)
C12P 21/06 (2006.01)
C07K 14/00 (2006.01)
C07H 21/02 (2006.01)

(52) U.S. Cl. .................. 435/471; 435/69.1; 435/183; 435/252.3; 435/320.1; 530/350; 536/23.1

(58) Field of Classification Search ............... None
See application file for complete search history.

(56) References Cited

U.S. PATENT DOCUMENTS

| 3,960,832 | A | 6/1976 | Kang et al. ............ 260/209 R |
| 4,326,052 | A | 4/1982 | Kang et al. ................ 536/1 |
| 4,326,053 | A | 4/1982 | Kang et al. ................ 536/1 |
| 4,331,440 | A | 5/1982 | Racciato .................. 8/495 |
| 4,342,866 | A | 8/1982 | Kang et al. .............. 536/119 |
| 4,377,636 | A | 3/1983 | Kang et al. .............. 435/101 |
| 4,385,123 | A | 5/1983 | Kang et al. .............. 435/253 |
| 4,401,760 | A | 8/1983 | Peik et al. ............... 435/101 |
| 4,529,797 | A | 7/1985 | Peik et al. ............... 536/123 |
| 4,535,153 | A | 8/1985 | Kang et al. .............. 536/123 |
| 4,874,044 | A | 10/1989 | Robison et al. ............ 166/275 |
| 5,175,278 | A | 12/1992 | Peik et al. ............... 536/123 |
| 5,175,279 | A | 12/1992 | Kurane et al. ............. 536/123 |
| 5,300,429 | A | 4/1994 | Baird et al. .............. 435/101 |
| 5,338,841 | A | 8/1994 | Pollock et al. ............ 536/23.7 |
| 5,854,034 | A | 12/1998 | Pollock et al. ............ 435/101 |
| 5,876,987 | A | 3/1999 | Champness et al. ........ 435/172.3 |
| 6,197,591 | B1 | 3/2001 | Stutzman-Engwall et al. ................ 435/486 |
| 6,551,795 | B1 | 4/2003 | Rubenfield et al. ......... 435/69.1 |
| 6,605,461 | B2 | 8/2003 | Yamazaki et al. ......... 435/252.1 |
| 2002/0035249 | A1 | 3/2002 | Yamazaki et al. .......... 536/123 |
| 2003/0233675 | A1 | 12/2003 | Cao et al. ............... 800/279 |
| 2009/0029443 | A1 | 1/2009 | Yamazaki ............... 435/252.3 |

FOREIGN PATENT DOCUMENTS

| EP | 0 728 841 A2 | 8/1996 |
| EP | 1 176 209 A1 | 1/2002 |
| WO | WO 01/64897 A2 | 9/2001 |
| WO | WO 2004/065426 A1 | 8/2004 |

OTHER PUBLICATIONS

Chica et al., "Semi-rational Approaches to Engineering Enzyme Activity: Combining the Benefits of Directed Evolution and Rational Design," *Curr. Opin. Biotechnol.*, 16(4):378-84, Aug. 2005.
Hoefler, A. C., "Introduction to Food Gums: Chemistry, Functionality, and Applications," *Hercules Incorporated, Food Gums Group*, Wilmington DE, http://www.herc.com/foodgums.index.htm, pp. 1-19.
Leung, et al., "Serological and Ecological Characteristics of a Nodule-Dominant Serotype from an Indigenous Soil Population of *Rhizobium leguminosarum* bv. Trifolii," *Appl. Environ. Microbiol.*, 60(2):408-15, Feb. 1994.
Pollock, T. J., "Gellan-related polysaccharides and the genus *Sphingomonas*," *J. Gen. Microbiol.*, 139(7):1939-45, 1993.
Pollock, T. J. et al., "Assignment of Biochemical Functions to Glycosyl Transferase Genes Which Are Essential for Biosynthesis of Exopolysaccharides in *Sphingomonas* Strain S88 and *Rhizobium leguminosarum*," *J. Bacteriol.*, 180(3):586-93, Feb. 1998.
Rubenfield et al. Accession ABD11054. Jul. 29, 2004.
Sakata, N. et al., "Study on New Viscosity Agent for Combination Use Type of Self-Compacting Concrete," *J. Advanced Concrete Technol.*, 1(1):37-41, Apr. 2003.
Seffernick et al., "Melamine Deaminase and Atrazine Chlorohydrolase: 98 Percent Identical but Functionally Different," *J. Bacteriol.*, 183(8):2405-10, Apr. 2001.
Videira, P. A. et al., "Identification of the *pgmG* Gene, Encoding a Bifunctional Protein with Phosphoglucomutase and Phosphomannomutase Activities, in the Gellan Gum-Producing Strain *Sphingomonas paucimobilis* ATCC 31461," *App. Environ. Microbiol.*, 66(5):2252-58, May 2000.
Witkowski et al., "Conversion of a Beta-ketoacyl Synthase to a Malonyl Decarboxylase by Replacement of the Active Site Cysteine with Glutamine," *Biochemistry*, 38(36):11643-50, Sep. 7, 1999.
CP Kelco, "Applications," retrieved Jul. 29, 2003, from http://cpkelco.com/applications/index.html.
CP Kelco, "Kelco-Crete®, Welan Gum," retrieved Apr. 25, 2003, from http://www.cpkelco.com/welan/molecular_structure.html.
CP Kelco, "Kelcogel®, Gellan Gum," retrieved Apr. 25, 2003, from http://www.cpkelco.com/gellan/food/molecular_structure.html.
CP Kelco, "Keltrol®, Xanthan Gum," retrieved Apr. 25, 2003, from http://www.cpkelco.com/xanthan/food/molecular_structure.html.
Yamazaki, "Compositions and Methods for Enhanced Bacterial Exopolysaccharide Production," U.S. Appl. No. 12/633,647, filed Dec. 8, 2009, 50 pages.

*Primary Examiner*—Christian L Fronda
(74) *Attorney, Agent, or Firm*—Seed IP Law Group PLLC

(57) ABSTRACT

The present invention provides nucleic acid sequences and variants thereof capable of modulating exopolysaccharide production in *Sphingomonas*, and provides methods of using such nucleic acid sequences to generate bacteria that hyperproduce exopolysaccharide in slime form.

5 Claims, 2 Drawing Sheets

METHODS FOR ENHANCED BACTERIAL EXOPOLYSACCHARIDE PRODUCTION

CROSS-REFERENCE TO RELATED APPLICATION

This application is a divisional of U.S. patent application Ser. No. 10/897,981, filed Jul. 23, 2004, now pending, which application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 850136_421D3_SEQUENCE_LISTING.txt. The text file is 13 KB, was created on Dec. 8, 2009, and is being submitted electronically via EFS-Web.

BACKGROUND OF THE INVENTION

1. Field of the Invention

The present invention relates generally to the production of exopolysaccharides, and more specifically, to a nucleic acid sequence and variants thereof capable of modulating exopolysaccharide production, and to the use of such nucleic acid sequences to generate bacteria that hyper-produce exopolysaccharide in slime form.

2. Description of the Related Art

There is an increasing demand for inexpensive and environmentally acceptable gelling agents for industrial applications and for the food industry. Some exemplary industrial applications of gelling agents include oil field drilling, adhesives, paints, animal feed, household products, personal care products (e.g., shampoo, lotion), oral care products (e.g., toothpaste), pharmaceuticals, and the like. Some exemplary uses of gelling agents in the food industry include use in pudding, dairy products, pie filling, dressings, confectionery, sauces, syrups, and the like. The biotechnology industry has responded to this demand for gelling agents by increasing the availability of a variety of bacterial exopolysaccharide products that are acceptable for commercial use.

Bacterial exopolysaccharides are useful compounds as gelling or viscosity increasing agents because of their distinctive rheological properties (e.g., resistance to shear, compatibility with various ionic compounds, stability to extreme temperatures, pH and salt concentrations). A variety of bacteria produce exopolysaccharides particularly useful as thickening or gelling agents. For example, a genus of bacteria that produces many types of exopolysaccharides is *Sphingomonas*. A few such polysaccharides include gellan, welan, rhamsan, S-7, and S-88 (see, e.g., Pollock, *J. Gen. Microbiol.* 139:1939, 1993). The exopolysaccharides produced by *Sphingomonas* are referred to as "sphingans," and at least three sphingans (gellan, welan, and rhamsan) are commercially produced by large-scale, submerged fermentation.

Many bacterial exopolysaccharide products offer a range of attractive improvements over synthetically produced materials, but they remain relatively expensive to produce because of the costs associated with recovery and purification of a desired product. Furthermore, conditions that allow for higher fermentation yields of exopolysaccharides also result in increased broth viscosity, which thickening ultimately requires higher energy input to effectively disperse oxygen and nutrients to allow sufficient bacterial growth in the fermentation broth. That is, fermentations that provide higher exopolysaccharide yields have also resulted in correspondingly higher production costs.

Hence, a need exists for a better understanding of bacterial biosynthesis of exopolysaccharide to aid in the identification of bacteria that produce more exopolysaccharide, and that produce exopolysaccharide in a form that does not increase the viscosity of a fermentation broth. In addition, a need exists for methods of making or identifying such bacteria, which in turn would allow optimization of exopolysaccharide production and yield under typical, industrial fermentation conditions. The present invention meets such needs, and further provides other related advantages.

BRIEF SUMMARY OF THE INVENTION

The present invention relates generally to the use of a nucleic acid sequence and variants thereof capable of modulating exopolysaccharide production, and to methods of using such nucleic acid sequences to generate bacteria that hyper-produce exopolysaccharide in slime form.

In one aspect, the present invention provides an isolated nucleic acid molecule comprising a sequence that remains hybridized under highly stringent conditions to a probe, wherein the probe consists of SEQ ID NO:1 or a complement of SEQ ID NO:1. In one embodiment, the aforementioned isolated nucleic acid molecules wherein said nucleic acid molecules encode at least one polypeptide capable of altering exopolysaccharide production in a *Sphingomonas* species. In related embodiments, the at least one encoded polypeptide comprises an amino acid sequence that is at least 80% identical to SEQ ID NO:2, or the encoded polypeptide comprises an amino acid sequence of SEQ ID NO:2 with conservative amino acid substitutions, or the polypeptide comprises the amino acid sequence of SEQ ID NO:2, or the polypeptide consists of the amino acid sequence of SEQ ID NO:2. In still another embodiment, the invention provides an isolated nucleic acid molecule comprising a nucleotide sequence as set forth in SEQ ID NO:1 or a complement of SEQ ID NO:1. In yet other embodiments, any of the aforementioned nucleic acid molecules are DNA or RNA.

In another embodiment, the invention provides a recombinant expression vector comprising at least one promoter operably linked to anyone of the aforementioned nucleic acid molecules. In still another embodiment, the recombinant expression vector expresses the modulator polypeptide as a fusion protein comprising a polypeptide product encoded by a second nucleic acid sequence, such as a tag or an enzyme. In certain embodiments, the recombinant expression vector has a regulated promoter. In still other embodiments, the recombinant expression vector is a plasmid. In yet another embodiment, the recombinant expression vector is plasmid X026 or plasmid X029 (ATCC PTA-5127). In one embodiment, the recombinant expression vector comprises at least one promoter operably linked to a nucleic acid molecule that comprises a nucleotide sequence as set forth in SEQ ID NO:1.

In still another embodiment, the present invention relates to a host cell comprising any of the aforementioned recombinant expression vectors. In certain embodiments, the host cell is a prokaryotic cell, such as a sphingan-producing bacterium or a *Sphingomonas* cell or a sphingan-producing *Sphingomonas* bacterium. In other embodiments, the host cell is a *Sphingomonas* bacterium capable of producing a sphingan such as gellan, welan, rhamsan, diutan, alcalan, S7, S88, S198, and NW11. In still other embodiments, the host cell produces a sphingan in capsule form or slime form. In certain embodiments, the host cell is *Sphingomonas* strain α252 (ATCC PTA-5128, Welam Slime), X287 (ATCC PTA-3487, Gellan Slime), X530 (ATCC PTA-3486), Z473 (ATCC PTA-3485), X031 (ATCC PTA-3488), or α27. In a related embodiment, the host cell is a xanthan-producing bacterium, such as a *Xanthomonas* bacterium and more specifically *Xanthomonas* strains X59 (ATCC 55298), X55 (ATCC 13951), α287, α300, or α301. In certain embodiments, the polypeptide or fusion protein expressed from the nucleic acid on the recombinant expression vector alters the level of exopolysaccharide production in the host cell.

In yet another aspect, the invention provides an isolated bacterium that produces exopolysaccharide, comprising a bacterium capable of producing exopolysaccharide in slime form even when expressing a polypeptide encoded by any of the aforementioned nucleic acid molecules and wherein the bacteria are any of the aforementioned bacteria, including a mutant of *Sphingomonas* strain α027; or a mutant of *Xanthomonas* strains α287, α300, or α301. In other embodiments, the bacterium that produces exopolysaccharide in slime form when expressing at least one polypeptide encoded by any of the aforementioned nucleic acid molecules is strain α062 (ATCC PTA-4426), α063, α065, or α069 or *Xanthomonas* strains α449 (ATCC PTA-5064), α485, or α525. In yet other embodiments, the invention provides an isolated bacterium selected from *Sphingomonas* strain α062 (ATCC PTA-4426), α063, α065, or α069 and mutants or derivatives thereof, wherein the bacteria are capable of producing an exopolysaccharide in slime form even when expressing at least one polypeptide encoded by any of the aforementioned nucleic acid molecules, and mixtures thereof of such bacteria. In still other embodiments, the invention provides an isolated bacterium selected from *Xanthomonas* strain α449 (ATCC PTA-5064), α485, or α525, and mutants or derivatives thereof, wherein the bacteria are capable of producing an exopolysaccharide in slime form even when expressing at least one polypeptide encoded by any of the aforementioned nucleic acid molecules, and mixtures thereof.

It is another aspect of the invention to provide a method for hyper-producing exopolysaccharide, comprising culturing bacteria under conditions and for a time sufficient to permit exopolysaccharide production, wherein the bacteria hyper-produce exopolysaccharide in slime form when expressing at least one polypeptide encoded by any of the aforementioned nucleic acid molecules; and separating the exopolysaccharide in slime form from such a culture. In certain embodiments, the bacteria are *Sphingomonas* bacteria, such as those capable of hyper-producing an exopolysaccharide selected from gellan, welan, rhamsan, diutan, alcalan, S7, S88, S198, and NW11, including *Sphingomonas* strains α062 (ATCC PTA-4426), α063, α065 and α069. In certain other embodiments, the bacteria are *Xanthomonas* bacteria, such as those capable of hyper-producing xanthan, including *Xanthomonas* strains α449 (ATCC PTA-5064), α485, and α525. Also provided are any of the aforementioned methods wherein the culturing comprises fermentation, or wherein the bacteria produce from about 20 grams to about 60 grams of exopolysaccharide per liter of culture. In some embodiments, the fermentation is conducted from about 48 hours to about 96 hours at a temperature ranging from about 25° C. to about 35° C. In still other embodiments, the invention provides any of the aforementioned methods wherein the separating of exopolysaccharide from the bacteria is by alcohol precipitation, such as by adding about 1 to about 1.5 culture volumes of alcohol to the culture. In other embodiments, the fermentation culture will have a viscosity ranging from about 15,000 cp to about 40,000 cp.

Turning to another aspect, the invention provides a method for making bacteria capable of hyper-producing an exopolysaccharide in slime form, comprising contacting bacteria suppressed for production of an exopolysaccharide in slime form with a mutagen, wherein the bacteria (i) contain a recombinant expression vector comprising at least one promoter operably linked to a nucleic acid molecule that encodes a polypeptide encoded by a nucleic acid molecule according to any one of claim 2 to 4, and (ii) express a polypeptide of part (i) such that exopolysaccharide production is suppressed; and identifying there from bacteria capable of hyper-producing exopolysaccharide in slime form in the presence of a polypeptide capable of suppressing exopolysaccharide production. In certain embodiments, there is provided a method for making bacteria that are capable of hyper-producing an exopolysaccharide in slime form, comprising (A) contacting (a) a mutagen with (b) bacteria that are capable of producing an exopolysaccharide in slime form, wherein the bacteria (i) contain a recombinant expression vector comprising at least one promoter operably linked to a nucleic acid molecule that encodes at least one polypeptide, wherein the nucleic acid molecule is any of the aforementioned nucleotide sequences, and (ii) express said at least one polypeptide of (i) such that exopolysaccharide production is suppressed, under conditions and for a time sufficient to produce mutagenized bacteria; and (B) identifying among said mutagenized bacteria one or a plurality of bacteria that are capable of hyper-producing exopolysaccharide in slime form. In one embodiment, the mutagen used in this method is ethylmethane sulfonate and the bacteria are *Sphingomonas* bacteria, such as those capable of producing an exopolysaccharide selected from gellan, welan, rhamsan, diutan, alcalan, S7, S88, S198, and NW11, including *Sphingomonas* strain α027.

In another aspect, the invention provides a bacterium produced by any one of the aforementioned methods, including a mutant of *Sphingomonas* strain α027, such as α062 (ATCC PTA-4426), α063, α065, or α069, and a mutant of *xanthomonas* strain α300, such as α449 (ATCC PTA-5046), α485, or α525.

DETAILED DESCRIPTION OF THE INVENTION

Figure 1:
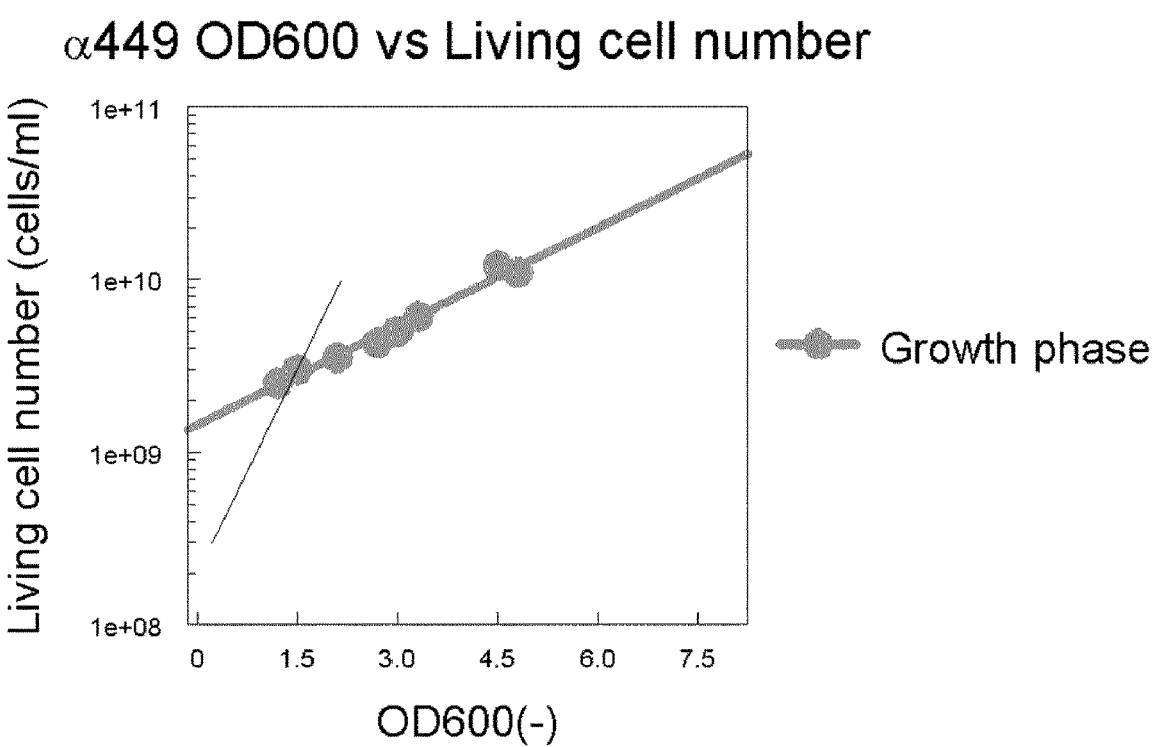
FIG. 1 shows the relation between living cell number and $OD_{600}$ of *Sphingomonas* strain α449 culture.

As described herein, the present invention provides nucleic acid molecules that encode a modulator of exopolysaccharide biosynthesis, and methods of making and using the same to identify bacteria that no longer respond to the modulator and, therefore, are capable of producing higher levels of exopolysaccharide. Use of genetic techniques to create improved exopolysaccharide producing bacteria is desired for the ease of large-scale production of biopolymers, such as sphingan polysaccharides. However, the synthesis of biopolymers is highly regulated because bacterial survival will be compromised if an unnecessary expenditure of metabolic energy synthesizing such large molecules occurs at a time, for example, when energy must be directed to growth. Moreover, the regulation of exopolysaccharide synthesis and assembly is very complex because a large number of proteins are required to create and export these macromolecules. The present invention solves these problem by identifying and using a nucleic acid sequence that encodes a negative regulator of sphingan biosynthesis to generate *Sphingomonas* derivatives that no longer respond to the negative regulator and that, consequently, are capable of producing higher than normal amounts of sphingan exopolysaccharide.

In the present description, any concentration range, percentage range, or integer range is to be understood to include the value of any integer within the recited range and, when appropriate, fractions thereof (such as one tenth and one hundredth of an integer), unless otherwise indicated. As used herein, "about" or "comprising essentially of" mean±15%. The use of the alternative (e.g., "or") should be understood to mean either one, both or any combination thereof of the alternatives. When a term is provided in the singular, the inventors also contemplate the plural of that term. In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present invention.

Sphingan Polysaccharides

The term "sphingan" and the phrase "sphingan exopolysaccharide," as used herein, refer to a group of related, but distinct, polysaccharides secreted by members of the genus *Sphingomonas* (Pollock, *J. Gen. Microbiol.* 139: 1939-1945, 1993). Common members of the genus *Sphingomonas*, and the sphingans they produce, include *Sphingomonas paucimobilis* (ATCC 31461, formerly *Pseudomonas elodea*), which produces exopolysaccharide S-60 (gellan) (see, e.g., U.S. Pat. Nos. 4,377,636; 4,326,053; 4,326,052 and 4,385,123); *Sphingomonas* sp. ATCC 21423, which produces exopolysaccharide S-7 (see, e.g., U.S. Pat. No. 3,960,832); *Sphingomonas* sp. ATCC 31554, which produces exopolysaccharide S-88 (see, e.g., U.S. Pat. Nos. 4,331, 440 and 4,535,153); *Sphingomonas* sp. ATCC 31555, which produces exopolysaccharide S-130 (welan) (see, e.g., U.S. Pat. No. 4,342,866); *Sphingomonas* sp. ATCC 31961, which produces exopolysaccharide S-194 (rhamsan) (see, e.g., U.S. Pat. No. 4,401,760); *Sphingomonas* sp. ATCC 31853, which produces exopolysaccharide S-198 (see, e.g., U.S. Pat. No. 4,529,797); *Sphingomonas* sp. ATCC 53159, which produces exopolysaccharide S-657 (diutan) (see, e.g., U.S. Pat. No. 5,175,278); *Sphingomonas* sp. ATCC 53272, which produces exopolysaccharide NW11 (see, e.g., U.S. Pat. No. 4,874, 044); *Sphingomonas* sp. FERM BP-2015 (previously *Alcaligenes latus* B-16), which produces biopolymer B-16 (alcalan) (see, e.g., U.S. Pat. No. 5,175,279); and the like.

The structures of the sphingans are all somewhat related. The main chain of each sphingan consists of a related sequence of four sugars, including D-glucose, D-glucuronic acid, L-mannose, and L-rhamnose. Polysaccharide members of the sphingan group are distinguishable from each other by virtue of the carbohydrates that form the polymer backbone, the presence or absence of acyl substituents (e.g., acetyl, glyceryl, pyruvyl, hydroxybutanoyl), and the presence or absence of side-chains. For example, sphingan polysaccharides may contain carbohydrate side-chains, and acetyl or pyruvyl groups attached to the polymer backbone carbohydrate. See, e.g., Mikolajczak et al., *Appl. Env. Microbiol.* 60:402, 1994. In certain embodiments, members of the sphingan exopolysaccharide family may be represented by the following general repeating chemical structure:

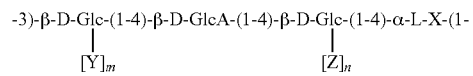

wherein Glc is glucose; GlcA is glucuronic acid or 2-deoxyglucuronic acid; Rha is rhamnose; Man is mannose; X may be Rha or Man; Z is attached to Glc residue 2 and may be α-L-Rha-(1-4)-α-L-Rha, α-L-Man, or α-L-Rha; Y is attached to Glc residue 1 and may be 13-D-Glc-(1-6)-α-D-Glc, 13-D-Glc-(1-6)-β-D-Glc, or α-L-Rha, subscripts m and n may be independently from 0 to about 1, and wherein the "reducing end" of the polymer is toward the X residue of the backbone. In standard practice, the reducing end of an oligosaccharide or polysaccharide is placed on the right. As used herein, the term "backbone" or "main chain" refers to that portion of the structure that excludes chains Y and Z (i.e., when m and n are equal to 0). For example, the main chain of gellan (S-60) comprises the sugars D-glucose, D-glucuronic acid and L-rhamnose in a 2:1:1 molar ratio, which are linked together to form a tetrasaccharide repeat unit with the following subunit order: glucose, glucuronic acid, glucose, rhamnose. The main chain of another sphingan, diutan (S-657), differs from gellan in that it has an additional disaccharide side chain of L-rhamnose attached to glucose residue 2, which forms a hexapolysaccharide repeat unit. Still another sphingan, welan (S-130), has the same primary structure as gellan but with a side chain of a single L-mannose or a single L-rhamnose attached to glucose residue 2, which forms a pentapolysaccharide repeat unit.

Some members of the sphingan polysaccharide family are acetylated at various positions. For example, as described herein, gellan (also referred to as "gellan gum") has the same carbohydrate backbone as welan (i.e., X=Rha), lacks a side chain sugar as welan has (i.e., m=0 and n=0), and, in contrast to welan, glucose residue 1 is fully glycerylated and partially acetylated. Gellan gum has, on average, about one glyceryl group per tetrasaccharide repeat unit and about one acetyl group per two repeat units. Another sphingan containing acyl groups is diutan (S-657), which contains acetyl groups at position 2 and/or position 6 of glucose residue 2. As is known in the art and described herein, sphingan polysaccharides may be subjected to conditions that promote deacylation in a conventional manner to remove the acyl groups. Thus, "deacylated," as used herein, refers to a sphingan polysaccharide that lacks one or more acyl substituents, such as glyceryl and acetyl groups.

By way of background, *Sphingomonas* can produce a sphingan exopolysaccharide in the form of a capsule or in the form of slime. As used herein, "capsule" refers to a polysaccharide attached to the surface of a producing bacterial cell, which remains attached to the cells even after aqueous dilution, sedimentation, or centrifugation. Typically, some form of physical (e.g., heat) or chemical treatment is required to separate capsule exopolysaccharide from a bacterial cell. As used herein, "slime" refers to a polysaccharide that is not attached to the producing bacterial cell. That is, exopolysaccharide in slime form can be substantially separated from bacterial cells by, for example, centrifugation of the fermentation broth or aqueous dilution of the broth (even in the absence of heat treatment or other physical or chemical treatment). As is known in the art, slime form exopolysaccharide producing bacteria can be distinguished from those producing capsular polysaccharide by observation with a light microscope: encapsulated *Sphingomonas* form multicellular aggregates, while slime-forming bacteria are evenly dispersed. In addition, an encapsulated *Sphingomonas* can be converted into a slimy *Sphingomonas* by, for example, mutagenesis as described in U.S. Pat. No. 6,605,461.

The term "*Sphingomonas*," as used herein, refers to a genus of gram-negative bacteria and derivative strains thereof that produce exopolysaccharides (e.g., sphingans), as described herein. The sphingan-producing family of gram-negative bacteria was first identified as belonging to the genus *Sphingomonas* in 1993 (see Pollock, *J. Gen. Microb.* 139: 1939, 1993). *Sphingomonas* useful in the present invention include parent *Sphingomonas* strains and derivatives thereof. As used herein, "parent strain" refers to bacteria or an individual bacterium before any treatment, such as chemical, biological or other types of mutagenesis, that will modify the genetic content (e.g., a substitution, insertion, or deletion within a genomic or extragenomic sequence) or phenotype of a parent strain. A person having ordinary skill in the art will understand that a mutant *Sphingomonas* can be a "parent strain," such as a mutant *Sphingomonas* derivative that subsequent to undergoing mutation produces exopolysaccharide in slime form rather than capsule form. As used herein, the term "derivative," when referring to a *Sphingomonas* species, strain, or bacterium, means any *Sphingomonas* species, strain, or bacterium that retains essentially the same or an enhanced capability of producing a sphingan exopolysaccharide, as described herein.

In addition, as used herein, "genetically mutated," "genetically modified," "mutagenized," and "mutant" refer to the quality of having one or more spontaneous or induced mutations, and of exhibiting properties that distinguish the mutated bacterium or strain from the parent bacterium or strain. Thus, a mutant *Sphingomonas* species, strain, or bacterium that hyper-produces a sphingan exopolysaccharide is contemplated as a derivative of the parent *Sphingomonas* species, strain, or bacterium for purposes of the present invention. "Induced mutagenesis," as used herein, means the treatment of bacterial cells with agents commonly known to induce a genetic alteration in DNA, including chemical compounds, electromagnetic radiation, ionizing radiation, and biological agents (such as viruses, plasmids, insertion elements or transposons). In one preferred embodiment, the invention provides a mutated *Sphingomonas* that produces exopolysaccharide in the presence of a negative regulator of exopolysaccharide biosynthesis.

The term "biosynthesis" as used herein describes the biological production or synthesis of any type of macromolecule, such as a nucleic acid, a polypeptide, or a polysaccharide (e.g., sphingans of *Sphingomonas* or xanthans of *Xanthomonas*), which may include several biosynthetic steps to arrive at an intermediate or final product. For example, sphingan exopolysaccharides are synthesized from individual carbohydrate units in a series of steps controlled by a number of enzymes (e.g., glycosyl transferases) of the bacteria. The term "biomass" refers to the exopolysaccharide plus bacterial cells in a bacterial culture.

In certain embodiments, *Sphingomonas* of the present invention produce exopolysaccharide in slime form. For example, *Sphingomonas* strains genetically mutated to synthesize and export sphingan exopolysaccharides in a slime form can be used as the "parent strain" in the context of the instant invention. Examples of *Sphingomonas* parent strains that are useful in the present invention include strain X287 (ATCC PTA-3487), which produces gellan gum (S-60) in a slime form; strain X530 (ATCC PTA-3486) and α252 (ATCC PTA-5128), which produce welan gum (S-130) in a slime form; strain Z473 (ATCC PTA-3485), which produces exopolysaccharide S-88 in a slime form; and strain X031 (ATCC PTA-3488), which produces exopolysaccharide S-7 in a slime form (see, e.g., U.S. Pat. Nos. 5,338,841 and 6,605,461). One advantage of a *Sphingomonas* strain that produces sphingan exopolysaccharide in slime form is that the fermentation broth viscosity can be significantly reduced, which should allow accumulation of increased amounts of a desired polysaccharide. However, exemplary slime form *Sphingomonas* strain X287 (ATCC PTA-3487) produced gellan gum at a level similar to parent strain *Sphingomonas paucimobilis* (ATCC 31461), while still advantageously decreasing broth viscosity. Accordingly, one aspect of the invention is the identification of a nucleic acid sequence capable of modulating the expression of polysaccharides, such as sphingans.

Sphingan Biosynthesis Modulator

Many species of bacteria synthesize and secrete acidic polysaccharides if supplied with a readily convertible carbon source, such as glucose, and an adequate amount of oxygen. Several members of the bacterial genus *Sphingomonas* produce a variety of acidic polysaccharides, collectively known as sphingans. Under certain environmental situations, bacteria will conserve energy by minimizing exopolysaccharide production via a negative regulatory system. The present invention is directed generally to nucleic acid sequences that encode one or more polypeptides capable of altering (e.g., increasing or decreasing in a statistically significant manner) exopolysaccharide production in *Sphingomonas*. This invention also pertains to methods of making bacteria capable of hyper-producing an exopolysaccharide in slime form by screening for bacteria that no longer respond to the modulator of exopolysaccharide biosynthesis. Thus, in certain preferred embodiments of the instant invention, an isolated nucleic acid molecule that encodes one or more polypeptides capable of modulating exopolysaccharide production in *Sphingomonas* species is used to make mutant bacteria capable of hyper-producing (i.e., producing, in a statistically significant manner, a greater quantity than the parent strain) an exopolysaccharide, for example, in slime form.

Suitable nucleic acid molecules and polypeptides capable of modulating exopolysaccharide production include, but are not limited to, naturally occurring nucleic acid molecules and polypeptides, and derivatives or analogues thereof. A "purified peptide, polypeptide, or protein" or "purified nucleic acid molecule" are sequences that are individually essentially free from contaminating cellular components, such as carbohydrate, lipid, nucleic acid (DNA or RNA), or other proteinaceous impurities associated with the nucleic acid molecule or polypeptide in nature. Preferably, the purified nucleic acids and polypeptides are sufficiently free of contaminants for use in the chemical coupling reactions of the instant invention or for other uses as needed. An "isolated peptide, polypeptide, or protein" or "isolated nucleic acid molecule" are sequences that have been removed from their original environment, such as being separated from some or all of the co-existing materials in a natural environment (e.g., a natural environment may be an unaltered cell).

Standard molecular genetic techniques can be used to identify and isolate a nucleic acid encoding a modulator of exopolysaccharide biosynthesis. As used herein, "modulator" refers to a compound (naturally or non-naturally occurring), such as a biological macromolecule (e.g., nucleic acid, protein, non-peptide or organic molecule), that typically has activity (directly or indirectly) as an inhibitor or an activator (or both) in a biological process or processes (e.g., repressor, activator, sigma factor, antimicrobial agent, antisense molecule, interference molecule, enzyme, and the like) in assays or screens described herein. "Modulation" refers to the capacity of a compound to enhance or inhibit (or both) a functional property of a biological activity or process in a statistically significant manner (e.g., gene expression, enzyme activity, or receptor binding). For example, using methods well known in the art (see, e.g., Sambrook et al., *Molecular Cloning: A Laboratory Manual*, 2$^{nd}$ edition, Cold Spring Harbor Press, Cold Spring Harbor, N.Y., 1989), a genomic expression library from *Sphingomonas* sp. S-88 (ATCC 31554) can be constructed, transformed into bacteria that express exopolysaccharide in capsule or slime form (e.g., *Sphingomonas* strain X031), preferably slime form, and screened for recombinant bacteria that no longer express exopolysaccharide.

Using such methods for the instant invention, a nucleic acid molecule (of approximately 2,600 nucleotides, SEQ ID NO:3) was identified and isolated from a *Sphingomonas* sp. S-88 genome, which encodes one or more polypeptides that inhibit, directly or indirectly, sphingan biosynthesis. Furthermore, a fragment of 573 nucleotides (SEQ ID NO:1) isolated from SEQ ID NO:3 was identified as sufficient to inhibit sphingan biosynthesis in *Sphingomonas*, including in S-7, S-88, S-130, S-194, S-198, and NW11. SEQ ID NO:1 is also capable of inhibiting xanthan biosynthesis in *Xanthomonas* (e.g., *Xanthomonas campestris* X59, ATCC 55298). In a preferred embodiment, the modulator of exopolysaccharide biosynthesis is a nucleic acid molecule that encodes a polypeptide modulator, preferably the modulator is a negative regulator of exopolysaccharide biosynthesis. That is, a host cell that expresses a nucleic acid that encodes a negative regulator of exopolysaccharide biosynthesis will result in inhibition of expression of exopolysaccharide in that host cell.

By way of background and not wishing to be bound by theory, nucleic acid sequence analysis of SEQ ID NO:3 revealed that potentially three polypeptides are encoded by this sequence, including a homologue of 3-deoxy-D-arabino-heptulosonic acid-7-phosphate synthase (DAHPS), a new polypeptide referred to as MPG, and a new polypeptide referred to as SpsN. DAHPS is involved in aromatic amino acid biosynthesis. In addition, SEQ ID NO:1 encodes SpsN, MPG and the carboxy-terminal terminal end of DAHPS. Thus, and as described in greater detail herein, one or more of MPG and SpsN can function as a modulator, directly or indirectly, of sphingan and xanthan biosynthesis. Example 3 describes how the presence of an spsN nucleic acid sequence is necessary, and potentially sufficient, to inhibit certain bacterial exopolysaccharide biosynthesis. In a preferred embodiment, the invention provides a nucleic acid molecule as set forth in SEQ ID NO:3 or SEQ ID NO:1, which encodes at least one polypeptide capable of altering exopolysaccharide production in a *Sphingomonas* or *Xanthomonas* species. Furthermore, the instant invention should be understood to also pertain to a nucleic acid molecule as set forth in SEQ ID NO:3 or SEQ ID NO:1 that itself functions as a modulator or encodes another nucleic acid that functions as a modulator. Thus, in another preferred embodiment, there is provided a nucleic acid molecule as set forth in SEQ ID NO:3 or SEQ ID NO:1 that is capable of altering exopolysaccharide production in a *Sphingomonas* or *Xanthomonas* species.

While particular embodiments of isolated nucleic acids encoding a modulator of exopolysaccharide biosynthesis are depicted in SEQ ID NOS:3 and 1, within the context of the present invention, reference to one or more isolated nucleic acids includes variants of these sequences that are substantially similar in that they encode native or non-native proteins, polypeptides or peptides with similar structure and function to a modulator of exopolysaccharide biosynthesis, such as SEQ ID NO:4 or SEQ ID NO:2. As used herein, the nucleotide sequence is deemed to be "substantially similar" if: (a) the nucleotide sequence is derived from the coding region of SEQ ID NO:3 or 1 isolated from a *Sphingomonas* or *Xanthomonas* (including, for example, portions of the sequence or allelic variations of the sequences discussed above) and is capable of altering exopolysaccharide biosynthesis; (b) the nucleotide sequence is capable of hybridization to the nucleotide sequences of the present invention under moderate or high stringency; (c) the nucleotide sequences are degenerate (i.e., sequences which code for the same amino acids using a different codon sequences) as a result of the "wobble" in the genetic code for the nucleotide sequences defined in (a) or (b); or (d) is a complement of any of the sequences described in (a), (b) or (c). Polynucleotide variants may contain one or more substitutions, additions, deletions, and/or insertions such that the activity of the encoded polypeptide, preferably, is not substantially diminished, as described herein.

In one embodiment, preferred is an isolated nucleic acid molecule comprising a sequence that remains hybridized under highly stringent conditions to a probe, wherein the probe consists of SEQ ID NO:1 or a complement of SEQ ID NO:1. In a preferred embodiment, the present invention provides an isolated nucleic acid molecule that consists of SEQ ID NO:1 or a complement of SEQ ID NO:1. Certain isolated nucleic acids of the inventions are, therefore, useful for detecting the presence of a nucleic acid that encodes a modulator of exopolysaccharide biosynthesis or an analogue, homologue, or derivative thereof, or are useful for expressing a polypeptide capable of altering exopolysaccharide biosynthesis. As used herein, "nucleic acid molecule" or "polynucleotide" refers to a polymeric form of nucleotides of a least ten bases in length, either ribonucleotides or deoxynucleotides or a modified from of either type of nucleotide. The term includes single and double stranded forms of DNA or RNA or any of a number of known natural and non-natural chemical variants of nucleic acids, for instance, nucleic acids having greater resistance to degradation, such as those containing phosphorothioates. In certain embodiments, the nucleic acid molecules that encode a modulator of exopolysaccharide biosynthesis are DNA or RNA.

"Moderately stringent hybridization conditions" and "highly stringent hybridization conditions" are conditions of hybridization of a probe nucleotide sequence to a target nucleotide sequence according to established principles of nucleotide base-pairing and hydrogen bond formation wherein hybridization will only be readily detectable when a portion of the target sequence is substantially similar to the complement of the probe sequence. Hybridization conditions vary with probe size as well as with temperature, time, and salt concentration in a manner known to those having ordinary skill in the art. For example, moderate hybridization conditions for a 50 nucleotide probe would include hybridization overnight in a buffer containing 5×SSPE (1×SSPE=180 mM sodium chloride, 10 mM sodium phosphate, 1 mM EDTA (pH 7.7), 5×Denhardt's solution (100× Denhardt' s=2% (w/v) bovine serum albumin, 2% (w/v) Ficoll, 2% (w/v) polyvinylpyrrolidone) and 0.5% SDS incubated overnight at 55-60° C. Post-hybridization washes at moderate stringency are typically performed in 0.5×SSC (1×SSC=150 mM sodium chloride, 15 mM trisodium citrate) or in 0.5×SSPE at 55-60° C. Highly stringent hybridization conditions typically would include 2×SSPE overnight at 42° C., in the presence of 50% formamide, followed by one or more washes in about 0.1×SSC to about 0.2×SSC, and 0.1% SDS at 65° C. for 30 minutes or more.

The isolated nucleic acids encoding a modulator of exopolysaccharide biosynthesis according to this invention can be obtained using a variety of methods. For example, as described above, a nucleic acid molecule may be obtained from a cDNA or genomic expression library by screening with an antibody or antibodies reactive with an SpsN or MPG polypeptide (see, e.g., Sambrook et al., *Molecular Cloning: A Laboratory Manual*, Cold Spring Harbor, 1989; Ausubel et al., *Current Protocols in Molecular Biology*, Greene Publishing, 1987). Further, random-primed PCR can be employed (see, e.g., *Methods in Enzymol.* 254:275, 1995). In addition, variations of random-primed PCR can also be used, especially when a particular gene or gene family is desired. In one such method, one of the primers is a random primer and the other is a degenerate primer based on the amino acid sequence or nucleotide sequence encoding a modulator of exopolysaccharide biosynthesis.

Other methods may also be used to obtain isolated nucleic acid molecules that encode a modulator of exopolysaccharide biosynthesis. For example, a nucleic acid molecule can be isolated by using the sequence information provided herein to synthesize a probe that can be labeled, such as with a radioactive label, enzymatic label, protein label, fluorescent label, or the like, and hybridized to a genomic library or a cDNA library constructed in, for example, a phage, plasmid, phagemid, or viral vector designed for replication or expression in one or more selected host cells (see, e.g., Sambrook et al., supra; Ausubel et al., supra). DNA representing RNA or genomic nucleic acid sequence can also be obtained by amplification using sets of primers complementary to 5' and 3' sequences of the isolated nucleic acid sequences provided in SEQ ID NOS:1 and 3, or to variants thereof, as described above. For ease of cloning, restriction enzyme sites can also be incorporated into the primers. Thus, the present invention includes nucleic acid molecules that are useful as primers for use in PCR amplification procedures specific for the amplification of at least one mRNA or DNA encoding a modulator of exopolysaccharide biosynthesis, particularly in samples derived from *Sphingomonas* or *Xanthomonas* (for PCR procedures see, e.g., U.S. Pat. No. 4,683,195; U.S. Pat. No. 4,965,188; and Innis et al., PCR Strategies, Academic Press, San Diego, 1995). Such PCR amplification methods are known in the art and include primer extension PCR, real time PCR, reverse transcriptase PCR (Freeman et al., *BioTechniques* 26:112, 1999), inverse PCR (Triglia et al., *Nucleic Acids Res.* 16:8186, 1988), capture PCR (Lagerstrom et al., *PCR Methods Applic.* 1:111, 1991), differential primer extensions (WO 96/30545), and other PCR amplification methods known in the art or later developed (see, e.g., Innis et al., PCR Strategies, Academic Press, San Diego. 1995).

In operation, PCR methods generally include the use of primer molecules that are chemically synthesized, but they may be generated enzymatically or produced recombinantly. PCR primers generally comprise two nucleotide sequences, one with sense orientation (5'→3') and one with antisense orientation (3'→5'), employed under preferred conditions for identification of a specific gene or condition. The same PCR primers, nested sets of oligomers or a degenerate pool of oligomers can be employed under less stringent conditions for detection and/or quantitation of closely related DNA or RNA sequences. These nucleic acid molecules can also be used individually or in combination as probes to identify contactin mRNA or DNA molecules in a sample. These nucleic acid molecules include:

5'-GACGGATCCTTGCCGAGGTGCG-3', (SEQ ID NO: 5)

5'-CGACGGCCACTACTAGCGTTCGAACG-3', (SEQ ID NO: 6)

5'-GTCCGTCGGTATCTACGGCTTCGAACG-3', (SEQ ID NO: 7)

SEQ ID NO: 5 is a forward primer, while SEQ ID NO:6 and SEQ ID NO:7 are reverse primers.

The nucleic acid molecules of the present invention can be made by a variety of methods known in the art. For example, nucleic acid molecules can be made using synthetic procedures or molecular biology techniques known in the art (see, e.g., Sambrook et al., supra). The length of the nucleic acid molecules of the present invention can be readily chosen by one skilled in the art depending on the particular purpose that the nucleic acid molecule is to be used for. For PCR primers, the length of the nucleic acid molecule is preferably between about 10 nucleotides and about 50 nucleotides in length, more preferably between about 12 nucleotides and about 30 nucleotides in length, and most preferably between about 15 nucleotides and about 25 nucleotides in length. For probes, the length of the nucleic acid molecule is preferably between about 20 nucleotides and about 1,000 nucleotides in length, more preferably between about 100 nucleotides in length and about 500 nucleotides in length, and most preferably between about 150 nucleotides and about 400 nucleotides in length.

Variants (including alleles) of the isolated SEQ ID NOS:1 and 3 nucleic acid sequences provided herein can be readily obtained from natural variants (e.g., polymorphisms, mutants and other serotypes) either synthesized or constructed. Many methods have been developed for generating mutants (see, generally, Sambrook et al., supra; Ausubel et al., supra). Briefly, preferred methods for generating nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, such as *E. coli* or other prokaryotes, and yeast or other eukaryotes. Standard screening and vector amplification protocols are used to identify mutant sequences and obtain high yields.

Similarly, deletions or insertions of a nucleic acid molecule that encodes a modulator of exopolysaccharide biosynthesis may be constructed by any of a variety of known methods. For example, the sequence may be digested with restriction enzymes or nucleases and be religated such that sequences are deleted, added, or substituted. Similarly, a variety of transposons and other insertional elements may be used to make recombinants having deletions and insertions. Thus, in one example, an spsN mutant containing a Tn10Kan transposon in the spsN coding sequence, as described herein, can be made according to methodologies known in the art. Other means of generating variant sequences, also known in the art, may be employed without requiring undue experimentation (for examples see Sambrook et al., supra, and Ausubel et al., supra). Moreover, verification of variant sequences is typically accomplished by restriction enzyme mapping, sequence analysis, hybridization, and the like. Variants that encode a modulator of exopolysaccharide biosynthesis that are capable of altering exopolysaccharide biosynthesis are particularly useful in the context of this invention.

A person having ordinary skill in the art would appreciate that other spsN encoding sequences can be identified and isolated in a similar manner. For example, analogues or derivatives thereof of spsN, or spsN homologues from other species of *Sphingomonas* or other related bacteria (such as *Xanthomonas* or *Pseudomonas*) can be identified and isolated using assays described herein. Thus, in certain embodiments, preferred modulators of exopolysaccharide biosynthesis in *Sphingomonas* or *Xanthomonas* comprise a nucleic acid sequence as set forth in SEQ ID NO:3 or SEQ ID NO:1, and analogues or derivatives thereof of SEQ ID NO:3 or SEQ ID NO:1 that are capable of altering exopolysaccharide biosynthesis. As used herein, the terms "derivative" and "analogue" when referring to a modulator of exopolysaccharide biosynthesis, refer to any modulator of exopolysaccharide biosynthesis that retains essentially the same (at least 50%, and preferably greater than 70%, 80%, 90%, or 95%) or enhanced biological function or activity as such parent modulator, as noted above. The biological function or activity of such analogues and derivatives can be determined using standard methods (e.g., plate assay, gel analysis, transcription assay, translation assay), such as with the assays described herein and known in the art. For example, an analogue or derivative may be a proprotein that can be activated by cleavage, or may be a precursor that can be activated or stabilized by an amino acid modification, to produce an active modulator of exopolysaccharide biosynthesis. Alternatively, a modulator of exopolysaccharide biosynthesis and analogues or derivatives thereof can be identified by their ability to specifically bind to one or more anti-modulator antibodies.

Another example of an analogue or derivative includes a modulator of exopolysaccharide biosynthesis (e.g., SpsN) that has one or more conservative amino acid substitutions, as compared with the amino acid sequence of a naturally occurring modulator. Among the common amino acids, a "conservative amino acid substitution" is illustrated, for example, by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine, or a combination thereof. Furthermore, an analogue or derivative of a modulator may include, for example, non-protein amino acids, such as precursors of normal amino acids (e.g., homoserine and diaminopimelate), intermediates in catabolic pathways (e.g., pipecolic acid and D-enantiomers of normal amino acids), and amino acid analogues (e.g., azetidine-2-carboxylic acid, homoproline, and canavanine).

Yet other embodiments of analogues or derivatives include a modulator of exopolysaccharide biosynthesis that retains at least about 60% identity with the parent molecule (i.e., the "parent" molecule will depend on the starting point, whether the parent is, for example, wild-type SpsN or an analogue of SpsN), more preferably at least about 70%, 80%, 90%, and most preferably at least about 95%. As used herein, "percent identity" or "% identity" is the percentage value returned by comparing the whole of the subject polypeptide, peptide, or analogue or variant thereof sequence to a test sequence using a computer implemented algorithm, typically with default parameters. Sequence comparisons can be performed using any standard software program, such as those provided in the Lasergene® bioinformatics computing suite, which is produced by DNASTAR® (Madison, Wis.). References for algorithms, such as BLAST® or ALIGN, may be found in, for example, Altschul, *J. Mol. Biol.* 219:555-565, 1991; or Henikoff and Henikoff, *Proc. Natl. Acad. Sci. USA* 89:10915-10919, 1992; and preferably BLAST® is used (as used herein, BLAST® refers to one or more of the following search algorithms: BLASTn, MEGABLAST, BLASTp, PSI-BLAST, PHI-BLAST, BLASTx, tBLASTn, tBLASTx, RPS-BLAST, CDART, VecScreen, trace BLAST, and the like), which is available at the National Center for Biotechnology Information (NCBI, Bethesda, Md.) website (www.ncbi.nlm-.nih.gov/BLAST) and results compared to databases, such as GenBank®. Other methods for comparing multiple nucleotide or amino acid sequences by determining optimal alignment are well known to those of skill in the art (see, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in Methods in Gene Biotechnology, pages 123-151 (CRC Press, Inc. 1997); and Bishop (ed.), Guide to Human Genome Computing, $2^{nd}$ Edition, Academic Press, Inc., 1998).

As used herein, "similarity" between two or more peptides or polypeptides is generally determined by comparing the amino acid sequence of one peptide or polypeptide with one or more other peptides or polypeptides having conserved amino acid substitutions thereto. Further, as is known in the art, a consensus sequence may be determined for a group of homologues, analogues, or derivatives based on the amino acid sequence of a parent compound, such as MPG (SEQ ID NO:4) or SpsN (SEQ ID NO:2). In a preferred embodiment, the polypeptide modulator comprises the amino acid sequence of SEQ ID NO:2, and in an even more preferred embodiment the modulator consists of the amino acid sequence of SEQ ID NO:2.

An analogue or derivative may also be a fusion protein of a modulator of exopolysaccharide biosynthesis. Fusion proteins, or chimeras, include fusions of one or more modulators of exopolysaccharide biosynthesis with non-modulator peptides or polypeptides, such as a polypeptide tag (e.g., an epitope tag or 6×His tag), carrier, or enzyme. The peptides may also have a detectable label or "tag" (i.e., be labeled), such as with a radioactive label, a fluorescent label, a mass spectrometry tag, biotin, and the like.

Peptides may be produced by recombinant techniques and a variety of host systems are suitable for production of modulators of exopolysaccharide biosynthesis and analogues or derivatives thereof, including bacteria (e.g., *E. coli*), yeast (e.g., *Saccharomyces cerevisiae*), insect (e.g., Sf9), and mammalian cells (e.g., CHO, COS-7). Many expression vectors have been developed and are available for each of these hosts. In a preferred embodiment, vectors that are functional (i.e., capable of replicating) in bacteria are used in this invention, even more preferably the vectors are broad host range plasmids, such as pRK311 (Ditta et al., *Plasmid* 13:149, 1985) and pMMB(EH) (Fürste et al., *Gene* 48:119, 1986). However, at times, it may be preferable to have vectors that are functional in other hosts or more than one host. Vectors and procedures for cloning and expression in *E. coli* are discussed herein and, for example, in Sambrook et al. (1987) and in Ausubel et al. (1995).

"Vector" refers to a nucleic acid assembly that is capable of directing the expression of a desired polypeptide. The vector may include an expression control sequence (e.g., transcriptional promoter/enhancer elements) that is operably linked to the nucleic acid coding sequence or isolated nucleic acid molecule(s) of interest. The vector may be composed of DNA, RNA, or a combination of the two (e.g., a DNA-RNA chimera). Optionally, the vector may include a polyadenylation sequence, one or more restriction sites, as well as one or more selectable markers, such as neomycin phosphotransferase or hygromycin phosphotransferase, as needed. Additionally, depending on the host cell chosen and the vector employed, other genetic elements such as an origin of replication, additional nucleic acid restriction sites, enhancers, sequences conferring inducibility or repressibility of transcription, and selectable markers, may also be incorporated into the vectors described herein.

"Cloning vector" refers to nucleic acid molecules, such as a plasmid, cosmid, or bacteriophage, which are capable of replicating autonomously in a host cell. Cloning vectors typically contain one or a small number of restriction endonuclease recognition sites, at which foreign nucleotide sequences can be inserted in a determinable fashion without loss of an essential biological function of the vector. Cloning vectors also typically contain a marker gene (e.g., antibiotic resistance encoding gene) that is suitable for use in the identification and selection of cells transformed with the cloning vector. Marker genes typically encode proteins that provide resistance to antibiotics, such as tetracycline, kanamycin, ampicillin, and the like.

As used herein, "nucleic acid expression construct" refers to a nucleic acid molecule construct containing a nucleic acid sequence that is expressed in a host cell. Typically, expression of a nucleic acid sequence of interest is placed under the control of an expression control sequence (e.g., promoter), and optionally, under the control of at least one regulatory element. Such an expressed sequence is said to be "operably linked to" the promoter. Similarly, a regulatory element and a promoter are operably linked if the regulatory element alters (i.e., increases or decreases with statistical significance) the activity of the promoter. As used herein, "expression control sequence" refers to a nucleotide sequence that directs the transcription of a structural gene. Typically, an expression control sequence is located in the 5' region of a gene, proximal to the transcriptional start site of a structural gene. If an expression control sequence is an inducible promoter, then the rate of transcription may, for example, be increased by the addition of an inducing agent or decreased by the addition of an inhibiting agent. In contrast, an inducing or an inhibiting agent does not affect the rate of transcription of a constitutive promoter.

A person having ordinary skill in the art is capable of selecting a suitable expression control sequence and suitable host for expressing, for example, an isolated nucleic acid sequence encoding a peptide having the amino acid sequence of SEQ ID NO:4 or variants thereof, wherein the variants comprise amino acid sequences having conservative amino acid substitutions or having at least 80% sequence identity to SEQ ID NO:4, and wherein the variants are capable of altering exopolysaccharide biosynthesis. In a preferred embodiment, there is provided a recombinant expression vector comprising at least one promoter operably linked to a nucleic acid molecule as set forth in SEQ ID NO:1 or 3, or a variant thereof, that encodes at least one polypeptide capable of altering exopolysaccharide biosynthesis in *Sphingomonas*.

A DNA sequence encoding a modulator of exopolysaccharide biosynthesis may be introduced into an expression vector appropriate for a particular host. In certain embodiments, the nucleic acid sequence may be cloned into a vector or expression vector to generate a fusion protein. The fusion partner may be chosen to be a polypeptide tag, such that isolation of a fusion protein is facilitated. The fusion carrier may prevent modulator degradation by host proteases, or the fusion partner may further function to transport the fusion peptide to inclusion bodies, the periplasm, the outer membrane, or the extracellular environment. Thus, the instant invention contemplates a recombinant expression vector comprising at least one promoter operably linked to a nucleic acid molecule as set forth in SEQ ID NO:1 or 3 or a variant thereof that encodes at least one polypeptide, which is expressed as a fusion protein capable of altering exopolysaccharide biosynthesis in *Sphingomonas*. Typically, the protein portion fused to a modulator of exopolysaccharide biosynthesis will be encoded by a second nucleic acid sequence; preferably the second nucleic acid sequence encodes a polypeptide tag or an enzyme, as described herein and is known in the art. In certain embodiments, the expression vector promoter will preferably be regulated and, in certain circumstances, the vector will preferably be a plasmid that replicates in *Sphingomonas, Pseudomonas*, or *Xanthomonas*. In a preferred embodiment, the plasmid is pRK311 containing SEQ ID NO:1 (X029, ATCC PTA-5127) or SEQ ID NO:3.

As used herein, "host cell" refers to any prokaryotic or eukaryotic cell that contains either a cloning vector or a nucleic acid expression construct. This term also includes those prokaryotic or eukaryotic cells that have been recombinantly engineered to contain cloned nucleic acid sequence(s) in the chromosome or genome of the host cell. Preferably, a host cell is a prokaryotic cell, more preferably a bacterium, and even more preferably a *Sphingomonas, Xanthomonas*, or *Pseudomonas. Sphingomonas* being most preferred. In certain preferred embodiments, the host cell is a sphingan producing bacterium, such as *Sphingomonas* sp. that produce gellan, welan, rhamsan, diutan, alcalan, S-7, S-88, S-198, and NW11. In one embodiment, the present invention provides a host cell *Sphingomonas*, such as α027, containing plasmid X029 (ATCC PTA-5127). In another embodiment, the host cell is *Xanthomonas.*

Enhanced Exopolysaccharide Biosynthesis

According to another aspect of the present invention there are provided methods for identifying and isolating bacteria that are capable of over-producing exopolysaccharide. In particular, a modulator of exopolysaccharide biosynthesis can be used to identify exopolysaccharide-producing bacteria that no longer respond to the modulator of exopolysaccharide biosynthesis. For example, colonies of bacteria that produce exopolysaccharide will have a mucoid appearance on agar plates, while non-producers will have a non-mucoid appearance. Introduction of a recombinant expression vector that encodes a modulator of exopolysaccharide biosynthesis into an exopolysaccharide producing bacterium will suppress exopolysaccharide expression, which means the bacteria will have a non-mucoid appearance on agar plates. These suppressed strains can be screened for spontaneous mutants or induced mutants that are capable of expressing exopolysaccharide even in the presence of a modulator of exopolysaccharide biosynthesis.

Within certain embodiments, there is provided a method for making bacteria capable of hyper-producing an exopolysaccharide in slime form, comprising contacting bacteria suppressed for production of an exopolysaccharide in slime form with a mutagen, wherein the bacteria (i) contain a recombinant expression vector comprising at least one promoter operably linked to a nucleic acid molecule that encodes at least one polypeptide capable of altering exopolysaccharide production, and (ii) express a polypeptide of part (i) such that exopolysaccharide production is suppressed; and then identifying therefrom bacteria capable of hyper-producing exopolysaccharide in slime form in the presence of a polypeptide capable of suppressing exopolysaccharide production.

The term "hyper-producing" refers to the capability of a first bacterial strain that produce statistically significantly more exopolysaccharide than a second strain from which the first bacterial strain was directly or indirectly derived. A first bacterial strain is "directly derived" from a second bacterial strain if the first strain was obtained from a single cycle of mutagenesis and/or selection of the second strain. A first bacterial strain is "indirectly derived" from a second bacterial strain if the first strain was obtained from multiple cycles of mutagenesis and/or selection of the second strain.

In one preferred embodiment, there is provided a method for making bacteria that are capable of hyper-producing an exopolysaccharide in slime form, comprising (A) contacting (a) a mutagen with (b) bacteria that are capable of producing an exopolysaccharide in slime form, wherein the bacteria (i) contain a recombinant expression vector comprising at least one promoter operably linked to a nucleic acid molecule that encodes at least one polypeptide, wherein the nucleic acid molecule encodes at least one polypeptide capable of altering exopolysaccharide production, and (ii) express said at least one polypeptide of (i) such that exopolysaccharide production is suppressed, under conditions and for a time sufficient to produce mutagenized bacteria; and (B) identifying among said mutagenized bacteria one or a plurality of bacteria that are capable of hyper-producing exopolysaccharide in slime form. In certain preferred embodiments, the bacteria are *Sphingomonas*, such as S-60, S-7, S130, S-7, S-194, S-198, and NW11, and the mutagen is, for example, ethylmethane sulfonate (EMS), N-methyl-N'-nitro-N-nitrosoguanidine (MNNG) or another suitable mutagen as known in the art. In another preferred embodiment, the modulator of exopolysaccharide biosynthesis is encoded by SEQ ID NO:1 or 3, and preferably by a nucleic acid molecule comprising a sequence that encodes the amino acid sequence of SEQ ID NO:2 or 4. In one particularly preferred embodiment, the parent bacterium is *Sphingomonas* α027, and the mutant of α027 that no longer responds to a modulator of exopolysaccharide biosynthesis is *Sphingomonas* α062 (ATCC PTA-4426) (for more details, see Examples). In another embodiment, the parent bacterium is *Xanthomonas campestris* X59, and the mutant of X59 that no longer responds to a modulator of exopolysaccharide biosynthesis is *Xanthomonas campestris* α449 (ATCC PTA-5064). Preferably, the mutant strain produces (in a statistically significant manner) more exopolysaccharide than the parent strain, such as at least about 10% to about 20% more, preferably at least about 20% to about 30% more, and more preferably at least about 30% to about 40% more.

Production of Exopolysaccharides

Another aspect of the present invention relates to the enhanced production of exopolysaccharide. For example, to produce sphingan exopolysaccharide, genetically mutated *Sphingomonas* bacteria are cultured under suitable fermentation conditions, which are well known in the art and which are generally described in U.S. Pat. No. 5,854,034. Briefly, a suitable medium for culturing the genetically mutated *Sphingomonas* is an aqueous medium that generally contains a source of carbon such as, for example, carbohydrates including glucose, lactose, sucrose, maltose or maltodextrins; a nitrogen source such as, for example, inorganic ammonium, inorganic nitrate, organic amino acids or proteinaceous materials such as hydrolyzed yeast, soy flour or casein; distiller's solubles or corn steep liquor; inorganic salts and vitamins. A wide variety of fermentation media will support the bacterial production of sphingans according to the present invention. The carbohydrates are included in the fermentation broth in varying amounts, but usually between about 1% and about 5% by weight of the fermentation medium. The carbohydrates may be added all at once prior to fermentation or alternatively, during fermentation. The amount of nitrogen may range from about 0.01% to about 0.2% by weight of the aqueous medium. A single carbon source or nitrogen source may be used, as well as mixtures of these sources. Among the inorganic salts which find use in fermenting *Sphingomonas* are salts that contain sodium, potassium, ammonium, nitrate, calcium, phosphate, sulfate, chloride, carbonate and similar ions. Trace metals, such as magnesium, manganese, cobalt, iron, zinc, copper, molybdenum, iodide and borate, may also be advantageously included. Vitamins, such as biotin, folate, lipoate, niacinamide, pantothenate, pyridoxine, riboflavin, thiamin and vitamin B.sub.12 and mixtures thereof, may also be advantageously employed.

Generally, the fermentation can be carried out at temperatures between (and including) about 25° C. and 35° C., with optimum productivity obtained within a temperature range of about (and including) 28° C. to 32° C. The inoculum is prepared by standard methods of volume scale-up, including shaken flask cultures and small-scale submerged stirred fermentation. The medium for preparing the inoculum can be the same as the production medium or can be any one of several standard media well-known in the art, such as Luria broth or YM medium. The concentration of carbohydrate can be reduced in the seed cultures to less than about 1% by weight. More than one seed stage may be used to obtain the desired volume for inoculation. Typical inoculation volumes range from about 0.5% to about 10% of the total final fermentation volume. The fermentation vessel typically contains an agitator to stir the contents. The vessel may also have automatic pH and foaming controls. The production medium is added to the vessel and sterilized in place by heating. Alternatively, the carbohydrate or carbon source may be sterilized separately before addition. A previously grown seed culture is added to the cooled medium (generally, at the fermentation temperature of about 28° C. to about 32° C.) and the stirred culture is fermented for about 48 hours to about 96 hours, producing a broth having a viscosity of from about 15,000 centipoise (cp) to about 20,000 cp, and from about 10 to about 15 g/L sphingan exopolysaccharide in slime form. The fermentation of a corresponding parent *Sphingomonas* strain will typically provide a broth having a viscosity of from about 25,000 cp to about 50,000 cp.

In this aspect, the invention provides an exopolysaccharide in slime form obtained from *Sphingomonas* or *Xanthomonas* grown in submerged, stirred and aerated liquid culture. The concentration of dissolved oxygen in the liquid culture preferably exceeds about 5% of saturation of water after 24 hours of culturing. Similar fermentations with encapsulated strains resulted in 0% dissolved oxygen after 24 hours. The lower viscosity provided by the exopolysaccharide in slime form results in improved aeration which allows *Sphingomonas* to be productive in culture for a longer period of time. In another aspect of the present invention, fermentation may be carried out in a semi-batch process where bacteria from one fermentation are used as an inoculum for a subsequent fermentation. In this aspect, for example, *Sphingomonas* that have been separated from the exopolysaccharide which they produced may be added to a fresh fermentation broth, or a fresh fermentation broth may be added to the remaining *Sphingomonas*. Hence, this aspect of the invention precludes the need to provide a separate seed culture.

Recovery of exopolysaccharides, regardless of the conditions used to produce them, preferably involves a precipitation step. The precipitated exopolysaccharide may then recovered by centrifugation. A typical method for recovering gellan and welan gums is a follows. Immediately after fermentation, the culture broths are heated to at least 90° C. to kill the living bacteria. The exopolysaccharides are then separated from the culture broth by precipitation with approximately 2 volumes (i.e., culture volume equivalents) of isopropyl alcohol, and the precipitated polysaccharide fibers are collected, pressed, dried, and milled. The alcohol is removed by distillation. In this most simple process, the polysaccharide remains attached to the cells, such that when the dried and milled polysaccharide is resuspended in water, the solution is not transparent. In the case of gellan gum, additional steps can be introduced to purify the polysaccharide away from the bacterial cells so that the resuspended product is more transparent. Before the alcohol precipitation, the culture broth is centrifuged and/or filtered or both while the temperature is maintained above the critical transition temperature between a highly viscous state and a liquefied state that is amenable to centrifugation or filtration. These processes for different sphingans are disclosed in, for example, U.S. Pat. No. 4,326,052 (gellan); U.S. Pat. No. 4,326,053 (gellan); U.S. Pat. No. 4,342,866 (welan); U.S. Pat. No. 3,960,832 (S-7); and U.S. Pat. No. 4,535,153 (S-88).

In certain embodiments, the present invention provides a method for hyper-producing exopolysaccharide, comprising culturing bacteria under conditions and for a time sufficient to permit exopolysaccharide production, wherein the bacteria hyper-produce exopolysaccharide in slime form when expressing at least one polypeptide encoded by a nucleic acid molecule that is capable of altering exopolysaccharide production; and separating the exopolysaccharide in slime form from the culture. Preferably, the bacteria are *Sphingomonas*, such as those that produce gellan, welan, rhamsan, diutan, alcalan, S7, S88, S198, or NW11, more preferably *Sphingomonas* strains α062 (ATCC PTA-4426), α063, α065 and α069. In a preferred embodiment, the culturing is by fermentation and the bacteria produce from about 5 grams to about 80 grams of exopolysaccharide per liter of culture, more preferably from about 10 grams to about 70 grams, and even more preferably from about 20 grams to about 60 grams. Optimal conditions for the fermentation is from about 48 hours to about 96 hours at a temperature ranging from about 25° C. to about 35° C. Preferably, the exopolysaccharide is separated by alcohol precipitation, wherein about 1 to about 1.5 volumes of alcohol is preferably added to the culture. Preferably, the fermentation culture has a final viscosity ranging from about 5,000 cp to about 40,000 cp, more preferably from about 10,000 cp to about 35,000 cp, and most preferably from about 15,000 cp to about 30,000 cp.

All of the above U.S. patents, U.S. patent application publications, U.S. patent applications, foreign patents, foreign patent applications and non-patent publications referred to in this specification and/or listed in the Application Data Sheet, are incorporated herein by reference, as if set forth herein, in their entirety.

EXAMPLES

Example 1

Preparation of White, High Glucose Resistant *Sphingomonas*

*Sphingomonas* X287 (ATCC PTA-3487) was used to inoculate 50 ml ¼YM−, having either 1% or 5% glucose in 125 ml baffled flask at 30° C. for two weeks without shaking. No exopolysaccharide-negative mutants appeared when the culture was spread onto a ¼YM+ plate after such an extended incubation. The same culture was spread onto a plate of ¼YM having 10% Glucose. Isolated colonies (83) were selected and used to inoculate 2 ml ¼YM having 3% Glucose, and then incubated for 40 hrs at 30° C. with shaking at 300 rpm. These cultures were spread on high glucose plates, and 12 colonies chosen and saved as X729-X741. Six out of those twelve mutants were visually white mutants.

Colonies were used to inoculate 2 ml YM− in small tubes and shaken at 300 rpm for 24 hrs at 30° C. (referred to as seed-1). Then 100 μl of these cultures were used to inoculate 5 ml B10G3, which culture was placed at an angle and incubated at 300 rpm for 24 hrs (referred to as seed-2). Then 5 ml of seed-2 was added to 20 ml B10G3 into 125 ml baffled flask and incubated with shaking at 200 rpm during the first 17 hrs, and then 400 rpm up to 46 hrs. 10 g of the final broth was precipitated by 20 volumes isopropyl alcohol (IPA) at room temperature. The sample was dried at 60° C. under vacuum for 2 hrs.

High Glucose Resistant, White Mutants

|  | Final pH | $OD_{600}$ | DW (g/L) (Ave = 14.9 g/L) |
| --- | --- | --- | --- |
| X733white | 5.82 | 17.7 | 15.1 |
| X734white | 5.77 | 17.9 | 15.5 |
| X735white | 5.78 | 17.5 | 15.3 |
| X736white | 5.84 | 16.1 | 14.7 |
| X737white | 5.55 | 12.5 | 13.6 |
| X738white | 4.31 | 6.0 | 3.6 |
| X743white | 5.78 | 17.0 | 15.3 |
| X753 | 5.82 | 14.1 | 13.0 |

Parent Gellan Slime

|  | Final pH | $OD_{600}$ | DW (g/L) (Ave = 12.7 g/L) |
| --- | --- | --- | --- |
| X287-1 | 5.82 | 14.5 | 12.6 |
| X287-2 | 5.78 | 14.2 | 12.8 |
| X287-3 | 5.77 | 13.6 | 12.5 |
| X287-4 | 5.78 | 14.2 | 12.8 |

The strain X733 inoculated in 125 ml baffled flask and incubated for 48 hrs. The culture broth spread on ¼YM+ plate generated slimy-capsule form colonies and a few yellow color colonies. Color indicator shows a hint to predict the mutation stability in some extent. One of the white slimy colonies was selected and saved as X996.

The X996 was cultivated in 100 ml B10 containing 3% and 6% Glucose using 500 ml baffled flask at 160 rpm for 24 hrs with OA % inoculation.

| 24 hrs pH/OD600/Living cell number |  |
| --- | --- |
| B10 3% Glucose | $6.30/9.95/2.4 \times 10^{10}$ |
| B10 6% Glucose | $6.32/7.88/1.7 \times 10^{10}$ |

It was hard to cultivate this X996 mutant reproducibly when the inoculation rate was low. This mutant did not grow well when it incubated under high rate of agitation.

This X996 was incubated for 30 hrs in 30 ml B10 medium supplemented by 7% Glucose using 125 ml baffled flask.

Low rate of inoculation suppressed the X996 cell growth. This culture medium saved at room temperature for a week without shaking. Then the culture was spread onto ¼YM 10% glucose plate. The *Sphingomonas* α016-α018 were isolated on high glucose containing ¼YM plates.

Example 2

Identification of *Sphingomonas* No Longer Responsive to SpsN

This example describes identification of a DNA sequence that suppresses biosynthesis of sphingan and xanthan by the following steps: (1) making an expression library of *Sphingomonas* S-88 genomic DNA; (2) transforming the expression library into *Sphingomonas* S-7; and (3) screening for suppression of exopolysaccharide S-7 production in *Sphingomonas* S-7 (i.e., spread bacterial cultures on plates and observe colonies for non-mucoid appearance). Primers SEQ ID NO:5 (22mer), and SEQ ID NOS:6 and 7 (26 and 27mer, respectively) were made and used with template Z964 (pBluescriptKS-BH, 716 bp, which is a fragment from Z939 (pRK311-s88nc2, 2.7 Kb)) to produce a 573 base pair fragment (SEQ ID NO:1) encoding, inter alia, functional spsN. The 573 base pair PCR fragment (SEQ ID NO:1) was cloned into plasmid pRK311, and two independent clones (X026 and X029) were further tested as follows:

| Plasmid | Strain | | | | | | | |
|---|---|---|---|---|---|---|---|---|
| | S-7 | S-88 | NW11 | S-130 | S-194 | S-198 | NW11 | X59 |
| X025 | + | + | + | + | + | + | + | + |
| X026 | − | − | − | − | − | − | − | − |
| X028 | + | + | + | + | + | + | + | + |
| X029 | − | − | − | − | − | − | − | − |
| Z959-1 | + | + | + | + | + | + | + | + |
| Z959-2 | + | + | + | + | + | + | + | + |
| Z959-3 | + | + | + | + | + | + | + | + |
| Z967 | − | − | − | − | − | − | − | − |
| Z939 | − | − | − | − | − | − | − | − |

X025 = pRK311-MPG (385 bp, 22mer-26mer);
X026 = pRK311-MPG + SpsN (573 bp, 22mer-27mer);
X028 = pRK311-MPG (385 bp, 22mer-26mer);
X029 = pRK311-MPG + SpsN (573 bp, 22mer-27mer);
Z959-1 to -3 = independent clones having pRK311-s88nc2 EH2700bp spsN::Tn10Kn;
Z967 = pRK311-BH716bp;
+ means the transconjugants produce exopolysaccharide, and
− means transconjugants do not produce exopolysaccharide on a selection plate.

These results demonstrate that the nucleic acid molecules encoding SpsN (e.g., X029) were capable of inhibiting polymer synthesis in *Sphingomonas* S-7, S-130, S-194, S-198, S-88, NW11, and *Xanthomonas* X59.

From analysis of the sequenced amplicon, spsN (modulator of exopolysaccharide biosynthesis) was located downstream of DAHPS (3-deoxy-D-arabino-heptulosonic acid 7-phosphate synthase). DAHPS regulates aromatic amino acid biosynthesis. The active PCR product was cloned into pRK311 and called X029 (pRK311-spsN, Tet$^r$). This expression vector, which contains SEQ ID NO:1, was trans-conjugated into *Sphingomonas* α016, and named α027, which had a suppressed polymer production phenotype. Then this α027 was treated with EMS to find mutants that showed an exopolysaccharide-positive phenotype under drug pressure Tet (i.e., in the presence of X029, which encodes the modulator of exopolysaccharide biosynthesis, SpsN). Under these conditions, some of the exopolysaccharide-positive phenotype could be due to mutations in either SpsN or elsewhere. After selection under no drug condition to get rid of plasmid X029 (i.e., encoding SpsN), strains α061-α076 were selected and saved for further testing (e.g., biomass production). These strains were cultivated in grass tube that contain 4 ml B10 medium with 5% glucose for 24 hrs. Then 3 ml of those cultures were inoculated into 25 ml B10 seed medium with 3% glucose in 125 ml baffled flask at 300 rpm for 48 hrs. From the each flask, 10 g of culture broth was precipitated by 2 vol of IPA. Precipitated materials were dried at 60° C. for 6 hrs.

| | Dry Weight | |
|---|---|---|
| α061 | 13.18 g/L | |
| α062 | 13.94 | somewhat capsule-slime |
| α063 | 14.16 | slimy on plate |
| α064 | 11.85 | |
| α065 | 15.77 | slimy on plate |
| α066 | 12.13 | |
| α067 | 13.47 | |
| α068 | 13.66 | |
| α069 | 14.13 | slimy on plate |
| α070 | 13.94 | |
| α071 | 13.60 | |
| α072 | 12.81 | |
| α073 | 13.10 | |
| α074 | 12.06 | |
| α075 | 9.29 | |
| α076 | 10.86 | |

2 ml culture was inoculated into 30 ml B10 seed medium with 5% glucose in 125 ml baffled flask. It was incubated at 200 rpm for 40 hrs and at 300 rpm until 72 hrs.

The following table indicates that the mutants (i.e., α062, α063, and α065) produced more than 20% biomass than that of original X287 slime mutant.

| | OD$_{600}$ | pH | DW(g/L) | |
|---|---|---|---|---|
| 1 α062 | 11.5 | 5.72 | 14.0 | +24% (white slime) |
| 2 α063 | 12.6 | 5.71 | 13.9 | +23% (white slime) |
| 3 α065 | 11.1 | 5.57 | 14.3 | +27% (white slime) |
| 4 α016 | 12.5 | 5.71 | 13.1 | +16% (white slime) |
| 5 X287 | 10.1 | 5.73 | 11.3 | Base (Original slime) |

The components of the culture medium were as follows:

| B10Medium | Seed | Production |
|---|---|---|
| Glucose | 30 g/L | 45 g/L |
| NH$_4$NO$_3$ | 1 g/L | 1.25 g/L |
| MSP* | 1 g/L | 1.00 g/L |
| K$_2$HPO$_4$ | 3.2 g/L | 0.50 g/L |
| KH$_2$PO$_4$ | 1.6 g/L | |
| MgSO$_4$* | 0.2 g/L | 0.05 g/L |
| Trace minerals* | 1 ml/L | 1 ml/L |
| 4% Deformer* | | 1.5 ml/L |
| DI Water | 1 L | 1 L |

| | x1000 Trace Minerals | | x1000 conc | |
|---|---|---|---|---|
| 2703 mg | FeCl$_3$—6H$_2$O | 270.3 g/mol | 10 mM |
| 1363 mg | ZnCl$_2$ | 136.3 g/mol | 10 mM |
| 1979 mg | MnCl$_2$—4H$_2$O | 197.9 g/mol | 10 mM |
| 238 mg | CoCl$_2$—6H$_2$O | 237.93 g/mol | 1 mM |
| 242 mg | Na$_2$MoO$_4$—2H$_2$O | 241.95 g/mol | 1 mM |
| 250 mg | CuSo$_4$—5H$_2$O | 249.7 g/mol | 1 mM | to 1000 ml divide to 4 in 250 ml

Example 3

Comparison of Exopolysaccharide Productions Between a *Sphingomonas* Strain No Longer Responsive to SpsN and its Parent Strains The original slime strain X287 and α016 were compared with mutant α062 under several 42 L fermentation tests. 400 ml 24 hrs flask culture was prepared as 1% starting culture broth for those experiments. The strain ATCC31464, parent of X287, was used a capsule forming gellan wild type strain.

| 42L/70L-fermentation test (40 g/L Glucose) | | | |
|---|---|---|---|
| | 24 hrs | 48 hrs | 60 hrs |
| X287(G116) | 11.0 g/L-7980 cp | 21.8 g/L-16,000 cp | |
| α016(G118) | 9.6 g/L-5040 cp | 19.2 g/L-10,400 cp | 20.7 g/L-11,900 cp |
| α062(G120) | | 23.2 g/L-13,500 cp | |
| α062(G131) | 10.3 g/L-6650 cp | 22.8 g/L-13,100 cp | |

| 42L/70L-fermentation test (45*-50 g/L Glucose) | | | | |
|---|---|---|---|---|
| | 24 hrs | 48 hrs | 60 hrs | 72 hrs |
| α062(G121) | 6.6 g/L-4160 cp | 21.6 g/L-12,300 cp | | 26.1 g/L-18,000 cp |
| α062(G123) | 8.8 g/L-5210 cp | 21.7 g/L-15,800 cp | | 25.5 g/L-24,700 cp |
| α062(G131) | 6.9 g/L-3910 cp | 23.2 g/L-12,800 cp | 25.7 g/L-16,200 cp | |

The broth was precipitated by 2 volumes IPA and subsequently dried at 60° C. for 6 hours. The final viscosity was 4-12 rpm.

The fermentation scores (biomass yield) are as follows.

| X287 | Duration | Glucose | Biomass | residual Glc | broth viscosity |
|---|---|---|---|---|---|
| G115 | 70 hrs | 40 g/L | 18.4 g/L | 0 g/L | 16,400 cp |
| G116 | 48 hrs | 40 g/L | 21.8 g/L | 0.2 g/L | 16,000 cp |
| G100 | 70 hrs | 50 g/L | 22.9 g/L | 4.8 g/L | 27,700 cp |

| α016 | Time | Glucose | Biomass | residual Glc | broth viscosity |
|---|---|---|---|---|---|
| G118 | 60 hrs | 40 g/L | 20.7 g/L | 0.6 g/L | 11,900 cp |

| α062 | Time | Glucose | Biomass | residual Glc | broth viscosity |
|---|---|---|---|---|---|
| G120 | 48 hrs | 40 g/L | 23.1 g/L | 0 g/L | 13,500 cp |
| G131 | 48 hrs | 40 g/L | 22.8 g/L | 0 g/L | 13,100 cp |
| G132 | 48 hrs | 40 g/L | 22.7 g/L | 0.5 g/L | 14,400 cp |
| G127 | 53 hrs | 40 g/L | 23.7 g/L | 1.3 g/L | 13,700 cp |
| G121 | 72 hrs | 50 g/L | 26.1 g/L | 2.5 g/L | 18,000 cp |
| G122 | 71 hrs | 50 g/L | 25.9 g/L | 4.5 g/L | 19,900 cp |
| G128 | 60 hrs | 45 g/L | 25.7 g/L | 1.9 g/L | 17,500 cp |
| G139 | 72 hrs | 45 g/L | 26.3 g/L | 1.9 g/L | 18,200 cp |
| G141 | 59 hrs | 45 g/L | 26.4 g/L | 0 g/L | 15,300 cp |
| G158 | 57 hrs | 45 g/L | 26.4 g/L | 0.8 g/L | 15,800 cp |
| G161 | 72 hrs | 45 g/L | 26.2 g/L | 0.5 g/L | 21,700 cp |

| ATCC31461 | | Glucose | Biomass | residual Glc | broth viscosity |
|---|---|---|---|---|---|
| G157 | 72 hrs | 45 g/L | 22.1 g/L | 4.3 g/L | 48,100 cp |

Culture Broth of α062(G158) was compared with that of ATCC31461(G157). The results are shown in the following table.

| (45 g/L glucose) using 70L-fermentor | | |
|---|---|---|
| | Final Broth | |
| | α062 (G158) | ATCC31461 (G157) |
| Frozen | G149F | 061501C |
| Total Biomass (g/L) | 26.4 (59.7%) | 22.3 (54.8%) |
| Residual Glucose (g/L) | 0.8 | 4.3 |
| Breach debris (g/L) (PHB) | 9.1 (20.6%) | 6.8 (16.7%) |
| Duration (hrs) | 57 | 72 |
| pH (—) | 6.7 | 5.17 |
| $OD_{600}$ (—) | 23.4 | 27.3 |
| Viscosity (# 4 12-60 rpm) | 15,800-3620 | 48,100-ND |
| Living cells (cells/ml) | $1.6 \times 10^{10}$ | $9.0 \times 10^{8}$ (not accurate) |
| 5% KOH consumption (ml) | 1270 | >1690 |
| Broth appearance | Homogeneous slime | Not homogeneous |
| Broth DO (%) hit 0% | None | 36~39 hrs |

Example 4

Identification of *Xanyhomonas* No Longer Responsive to SpsN

The DNA sequence contains biopolymer suppression factor in X029 (ATCC PTA-5127) was transconjugated into *Xanthomonas campestris* X55(ATCC13951) and X59 (ATCC 55298) by mating. Polymer production suppressed colonies were isolated as α287, α300 and α301 on tetracycline containing selection plate.

This Xanthan Gum production suppressed α300 (X59: X029) transconjugant was treated with chemical mutagen EMS. Mutant colonies that do not respond to suppression factor X029 even under drug pressure were isolated first then drug sensitive mutants α449 (ATCC PTA-5064), α474, α485, α499, α501, α525, α526, α544 were selected under no drug pressure to get rid of the X029 suppression factor. Those mutants were incubated in 26 ml YM plus 3& glucose medium using 125 ml baffled flask for 48 hrs. Those mutants performance were shown in the following table.

| | | Comparison between X59 and its mutants | | | |
|---|---|---|---|---|---|
| | | 0/24/32/48 $OD_{600}$ | 0/24/32/48 pH | 24/32/48 hours DW (g/L) | |
| 1 | α449 | 0.31/7.86/7.62/9.24 | 6.27/7.28/6.87/5.43 | 9.8/12.0/16.4 | Ave = 16.0 |
| 2 | α474 | 0.27/6.70/6.19/5.79 | 6.31/7.48/7.04/6.37 | 9.9/11.2/15.6 | |
| 3 | α485 | 0.29/6.82/6.60/7.10 | 6.26/7.23/7.03/5.94 | 7.1/11.3/16.0 | |
| 4 | α499 | 0.28/6.99/6.43/6.34 | 6.25/7.40/7.07/6.10 | 8.1/10.8/15.7 | |
| 5 | α501 | 0.26/7.13/6.73/5.13 | 6.32/7.22/7.04/6.23 | 7.7/12.2/16.2 | |
| 6 | α525 | 0.28/6.99/6.84/8.34 | 6.29/7.32/7.09/6.01 | 7.5/11.0/16.3 | |
| 7 | α526 | 0.30/7.59/7.22/7.54 | 6.24/7.33/6.99/5.71 | 7.7/11.6/16.5 | |
| 8 | α544 | 0.24/7.52/5.99/4.99 | 6.28/7.27/7.11/6.57 | 7.3/9.3/15.5 | |
| 9 | X59 | 0.27/7.28/6.74/6.17 | 6.24/7.24/7.03/5.93 | 7.4/10.0/15.3 | Ave = 15.4 |
| 10 | X59 | 0.27/7.21/6.94/7.02 | 6.23/7.29/7.00/5.67 | 8.1/9.7/15.5 | |

| | | $OD_{600}$(0/24/32/48) | Living cell#(0/24/32/48) |
|---|---|---|---|
| 1 | α449 | 0.31/7.86/7.62/9.24 | $3.9 \times 10^8/8.9 \times 10^9/8.4 \times 10^9/1.0 \times 10^{10}$ |
| 2 | α474 | 0.27/6.70/6.19/5.79 | $3.9 \times 10^8/1.3 \times 10^{10}/4.6 \times 10^9/8.0 \times 10^9$ |
| 3 | α485 | 0.29/6.82/6.60/7.10 | $3.7 \times 10^8/9.3 \times 10^9/1.2 \times 10^{10}/8.4 \times 10^9$ |
| 4 | α499 | 0.28/6.99/6.43/6.34 | $4.5 \times 10^8/6.9 \times 10^9/5.7 \times 10^9/7.4 \times 10^9$ |
| 5 | α501 | 0.26/7.13/6.73/5.13 | $4.0 \times 10^8/1.0 \times 10^{10}/1.0 \times 10^{10}/7.4 \times 10^9$ |
| 6 | α525 | 0.28/6.99/6.84/8.34 | $3.7 \times 10^8/9.9 \times 10^9/6.0 \times 10^9/9.5 \times 10^9$ |
| 7 | α526 | 0.30/7.59/7.22/7.54 | $4.6 \times 10^8/1.0 \times 10^{10}/1.4 \times 10^{10}$/ND |
| 8 | α544 | 0.24/7.52/5.99/4.99 | $3.7 \times 10^8/7.8 \times 10^9/6.6 \times 10^9/1.3 \times 10^{10}$ |
| 9 | X59 | 0.27/7.28/6.74/6.17 | $3.6 \times 10^8/8.1 \times 10^9/9.0 \times 10^9/6.9 \times 10^9$ |
| 10 | X59 | 0.27/7.21/6.94/7.02 | $4.6 \times 10^8/8.7 \times 10^9/6.6 \times 10^9/6.8 \times 10^9$ |

α449 and α501 generated 10-20% more biomass than that of parent X59 in 32 hrs even with the same level of living cell number. This indicates that polymer accumulation speed of those mutants is faster than that of parent X59.

FIG. 1 shows relation between living cell number and $OD_{600}$ of α449 culture. To achieve optimum seed culture, cell numbers were maximized based upon $OD_{600}$ value for next stage of production fermentation.

Figure 2:
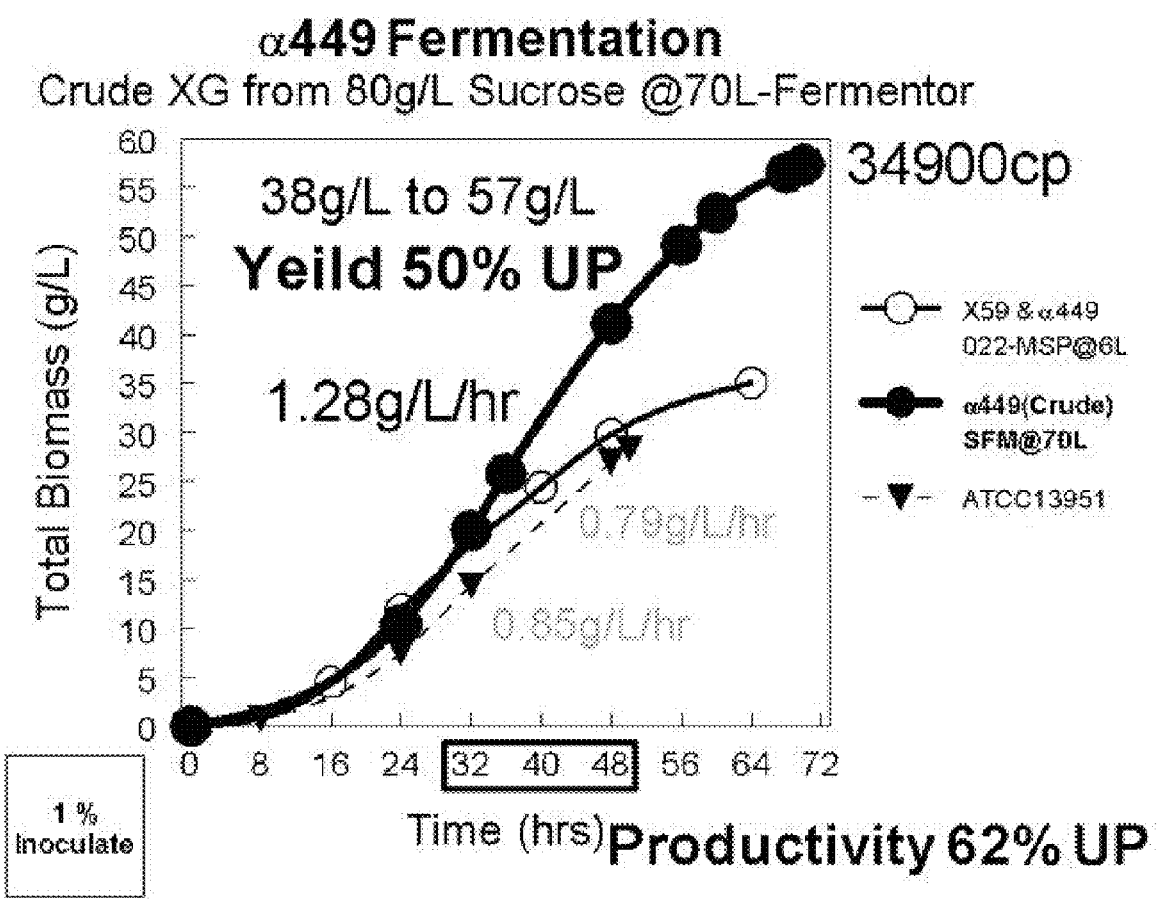
FIG. 2 shows α449 42 L production fermentation using SEB-022-SF+MSP medium.

FIG. 2 shows α449 42 L production fermentation using SEB-022-SF+MSP medium. The open circle represents xanthan gum production from fermentation of X59 or α449 in SEB-022-MSP in a 6 L fermentor; the solid circle represents biomass (including cells and xanthan gum) of fermentation of α449 using SEB-022-SF+MSP (also referred to as "SFM") in a 70 L fermentor; and the triangle represents xanthan gum production from fermentation of ATCC13951. The data of the ATCC13951 fermentation in FIG. 2 is from Letisse et al., *Applied Microbiology and Biotechnology* 55(4): 417-22, 2001. MSP refers to digested soy protein.

The final production yield was 57.3 g/L out of 80 g/L sucrose. This mutant did not respond to suppression factor X029 and accumulated higher level of Xanthan gum under the conditions of 28° C., dissolved oxygen (DO) at 30%, and pH6.5.

The α449 400 ml seed culture was inoculated into SEB-022-SF+MSP (Suc=80 g/L) medium and incubated for 70 hrs using 70 L fermentor. This medium contains 0.69 g/L total nitrogen (0.6 g/L from Soy and 0.09 g/L from MSP). The final broth OD was 11.3, pH was 6.55, and the living cell number was $2.0 \times 10^{10}$/ml. The final broth viscosity was 34,900 cp/16,300 cp/9,420 cp-12 rpm/30 rpm/60 rpm using No. 4 spindle by Brookfield viscometer.

The components of SEC-022-SF+MSP medium used in this example are as follows:

| | |
|---|---|
| Sucrose | 80.0 g/L |
| MSP | 1.0 g/L (N = 0.09) |
| $MgSO_4$ | 0.5 g/L |
| $K_2HPO_4$ | 2.0 g/L |
| Soy Protein | 7.6 g/L (N = 0.6) |
| 4% DF289 | 1 ml/L |
| Trace | 1 ml/L |

The components of SEC-022-MSP medium used in this example are as follows:

| | |
|---|---|
| Sucrose | 60.0 g/L |
| MSP | 1.0 g/L (N = 0.09) |
| $MgSO_4$ | 0.5 g/L |
| $K_2HPO_4$ | 2.0 g/L |
| Soy Protein | 7.6 g/L (N = 0.6) |
| 4% DF289 | 1 ml/L |
| Trace | 1 ml/L |

The invention claimed is:

1. A method for making a first strain of bacteria that are capable of hyper-producing an exopolysaccharide in slime form, comprising:
   (A) contacting, under conditions and for a time sufficient to produce mutagenized bacteria,
      (a) a mutagen,
   with
      (b) a second strain of bacteria that are capable of producing an exopolysaccharide in slime form, wherein the bacteria
         (i) contain a recombinant expression vector comprising at least one promoter operably linked to a nucleic acid molecule that encodes at least one polypeptide, wherein said nucleic acid molecule comprises a nucleotide sequence that is capable of hybridization to a probe under conditions that comprise exposure to 2×SSPE and 50% formamide at 42° C., wherein the probe consists of the nucleotide sequence set forth in SEQ ID NO:1 or a complement of SEQ ID NO:1, and wherein said at least one polypeptide comprises the amino acid sequence of SEQ ID NO:2 or a derivative thereof having at least about 95% sequence identity to SEQ ID NO:2, wherein the polypeptide inhibits sphingan production when present in a *Sphingomonas* species compared to sphingan production in an unmodified *Sphingomonas*, and
         (ii) express said at least one polypeptide of (i) such that exopolysaccharide production is suppressed,
      and thereby producing mutagenized bacteria; and
   (B) identifying among said mutagenized bacteria one or a plurality of bacteria that produce statistically significantly more exopolysaccharide than the second strain of bacteria and thereby obtaining said first strain of bacteria that are capable of hyper-producing exopolysaccharide in slime form.

2. The method of claim 1 wherein said mutagen is ethylmethane sulfonate.

3. The method according to claim 1 wherein said bacteria are *Sphingomonas* bacteria.

4. The method according to claim 3 wherein said *Sphingomonas* bacteria are capable of producing an exopolysaccharide selected from the group consisting of gellan, welan, rhamsan, diutan, alcalan, S7, S88, S198, and NW11.

5. The method according to claim 1 wherein said bacteria are *Xanthomonas* bacteria.

* * * * *

SEQUENCE LISTING

<160> NUMBER OF SEQ ID NOS: 11

<210> SEQ ID NO 1
<211> LENGTH: 573
<212> TYPE: DNA
<213> ORGANISM: Sphingomonas sp.

<400> SEQUENCE: 1
actagtggat ccttgccgag gtgcgcggct tcttcgccgt ccaccgcgcc gagggcacct      60
tcgccggcgg catccatgcc gagatgaccg gtcagaatgt gaccgagtgc accggcggcg     120
cgatcgcgat caccgagcag ggcctggccg atcgctacca cacgcattgc gacccgcggc     180
tcaacgcggg tcagagcctg gagctggcct tcctactcgc cgagatgctc aacgacgaaa     240
tggcggagcg tcgcaaggcc gccgcctgat gcccggcggc gcgttgctca gcggagcagc     300
gcgcccgcca gcgcccacag gccatagccg agcacgaaca ccagcattca ggcgatcacc     360
gcgctgccgg tgatgatcgc aagacgggtg cggaccgaga atttctcctc gcgcgcgcga     420
tcccagccct cgaccaccgg gggctgcggc gtgggcagcg gggtcttggg aaaggcgatc     480
ggcgtcgcga ccggtccggc cacggcggtc gtcaggtcgg catcggtcag cggcgtgacg     540
aattcgcagc catagatgcc gaagcttatc gat                                  573

<210> SEQ ID NO 2
<211> LENGTH: 60
<212> TYPE: PRT
<213> ORGANISM: Sphingomonas sp.

<400> SEQUENCE: 2

Met Ile Ala Arg Arg Val Arg Thr Glu Asn Phe Ser Ser Arg Ala Arg
 1               5                  10                  15

Ser Gln Pro Ser Thr Thr Gly Gly Cys Gly Val Gly Ser Gly Val Leu
            20                  25                  30

Gly Lys Ala Ile Gly Val Ala Thr Gly Pro Ala Thr Ala Val Val Arg
        35                  40                  45

Ser Ala Ser Val Ser Gly Val Thr Asn Ser Gln Pro
    50                  55                  60

<210> SEQ ID NO 3
<211> LENGTH: 2590
<212> TYPE: DNA
<213> ORGANISM: Sphingomonas sp.

<400> SEQUENCE: 3
ctgcaggaat tcgtcacgcc gctgaccgat gccgacctga cgaccgccgt ggccggaccg      60
gtcgcgacgc cgatcgcctt tcccaagacc ccgctgccca cgccgcagcc cccggtggtc     120
gagggctggg atcgcgcgcg cgaggagaaa ttctcggtcc gcacccgtct tgcgatcatc     180
accggcagcg cggtgatcgc ctggatgctg gtgttcgtgc tcggctatgg cctgtgggcg     240
ctggcgggcg cgctgctccg ctgagcaacg cgccgccggg catcaggcgg cggccttgcg     300
acgctccgcc atttcgtcgt tgagcatctc ggcgagtagg aaggccagct ccaggctctg     360
acccgcgttg agccgcgggt cgcaatgcgt gtggtagcga tcggccaggc cctgctcggt     420
gatcgcgatc gcgccgccgg tgcactcggt cacattctga ccggtcatct cggcatggat     480
gccgccggcg aagtgccct cggcgcggtg acggcgaag aagccgcgca cctcggcaag     540
gatccggtcg aacggccgcg tcttgtagcc gttcgcggcc ttgacgacgt tgccgtgcat     600

-continued

| | |
|---|---|
| cggatcgcag ctccacacca ccggatggcc ctcgcgcttc accgcgcgga ccagcttggg | 660 |
| caggcccgtc tcgatcttgt cgtggccata gcgcgtgatc agcgtcatgc ggccgggcac | 720 |
| gcggcccggg ttgagcgtgt cgagcagccg cagcagcgcg tcgggctcga ggctcggccc | 780 |
| gcacttcatc ccgatcggat tgccgatgcc cgcaggaaac tcgacatgcg ccgagccctc | 840 |
| gaagcgggtg cggtcgccga tccacaggaa gtgcgccgag gtatcgtacc agtcgcggt | 900 |
| caggctgtcc tgccgggtca gcgcctgctc ataggggagc agaagcgcct cgtggctggt | 960 |
| gtagaagtcg gtgcccttca gttgcggcac ggtatcgggg ttgatcccgc acgcctccat | 1020 |
| gaagtcgagc gcctcgccga tccggtcggc gacatcggcg aacttggccg ccaggggct | 1080 |
| cttgcccatg aaatcaagcg tccacttgtg cacctgatgc aggttcgcat agccgccacc | 1140 |
| cgcaaaggcg cgcagcagat tgagcgtcgc cgccgactgg ctgtagccct gcaccatccg | 1200 |
| ctgcggatcg gggatccgcg cctcgggcgt gaaggcgatg tcgttgacgt tatcgccgcg | 1260 |
| gtagctgggc agctcgacac cgtcgatcac ctcggtatcg gccgagcgcg gcttggcgaa | 1320 |
| ctggccggcc atccgtccga gcttcaccgt cggcagcttc gaggcgaagg tgaggaccac | 1380 |
| cgccatctgc aggatcacgc ggaaggtgtc gcggatgttg ttcggatgga actcggcgaa | 1440 |
| gctctcggcg cagtcgccgc cctggagcag gaaggcctcg ccgcgcgcga ccttgcccag | 1500 |
| ctcggtggtg agctcgcgcg cttctccggc gaagaccagc ggcggatagc tgctcagctg | 1560 |
| ccgggtggcg gcgtcgagcg cgctcttgtc cggatattgt ggcatctggc gcgcttcggc | 1620 |
| gcgcgtccag ctatcggggg tccagcttgc cattgcactc tccacgtcgc ggacggcgac | 1680 |
| gtgccagtcc gcatgctcgg cgattcccat cgccgcaatc tggttcatca ccttggtatt | 1740 |
| ggcgcgcttg ccgtcggtct cccagccctg cacggtagag cctggcgtgt cgaaccaggc | 1800 |
| accgaaggcg gcgcggctga gggtgcgttc ttcgcgatac tggcggatct tggaaccggc | 1860 |
| taacgtcgtc atcgccgagc cttacccggc aagggtaata gcgtgcaagg gaaaattacc | 1920 |
| cgatcagggt aatcgaatct ggctgcaatt gcgtcgggat ggcgccgggt gtagccgccg | 1980 |
| cgcaatggac ctattcgacg cacaggctcg cgaccttgcc gggctgacgg cgcggggccg | 2040 |
| ccgccggtcg ctgagcgctc gcgcgggcgc ggacttcgct tccaacgact atctcggcct | 2100 |
| ggccgattcc ccggcgctgc gcgcggcggt ggccgatgcg ttgcagcgcg gcgtgcccat | 2160 |
| cggctcgggt ggttctcggc tgctccgcgg caatcacccg gagcatgcgg cgctggaagc | 2220 |
| cgaagcagcg gccttttcg agcgcgagtc ggctttgtat ttttcgagcg gctatgccgc | 2280 |
| caatgccgcg gtgctcgcga ccttgccgca gcgcggcgat ctcgtgctgt tcgatgcgct | 2340 |
| tgttcatgca agcgcgcatg aggggatgcg gctcggccgg gcggagacgc ggcaggcggc | 2400 |
| gcacaacgac gtcgcggcct ttgccgaggc gattgccgcg tggcgaggcg aaggcggggc | 2460 |
| agggtgcgtg tggatcgccg tggagagcct gtacagcatg gacggtgata tcgcgccgct | 2520 |
| gcccgcgctt tccgcgctcg ccgaccgcga gaatgcgatc ctgctggtcg atccccggga | 2580 |
| attcgatatc | 2590 |

<210> SEQ ID NO 4
<211> LENGTH: 34
<212> TYPE: PRT
<213> ORGANISM: Sphingomonas sp.

<400> SEQUENCE: 4

```
Met Pro Gly Gly Ala Leu Leu Ser Gly Ala Ala Arg Pro Pro Ala Pro
 1               5                  10                  15
Thr Gly His Ser Arg Ala Arg Thr Pro Ala Phe Arg Arg Ser Pro Arg
            20                  25                  30
```

-continued

Cys Arg

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
gacggatcct tgccgaggtg cg                                    22

<210> SEQ ID NO 6
<211> LENGTH: 26
<212> TYPE: DNA
<213> ORGANISM: Artificial Sequence
<220> FEATURE:
<223> OTHER INFORMATION: PCR primer

<400> SEQUENCE: 6
cgacggccac tactagcgtt cgaacg                                26

<210> SEQ ID NO 7
<211> LENGTH: 27
<212> TYPE: DNA
<213> ORGANISM: Artificial Sequence
<220> FEATURE:
<223> OTHER INFORMATION: PCR primer

<400> SEQUENCE: 7
gtccgtcggt atctacggct tcgaacg                               27

<210> SEQ ID NO 8
<211> LENGTH: 529
<212> TYPE: PRT
<213> ORGANISM: Sphingomonas sp.

<400> SEQUENCE: 8

Met Thr Thr Leu Ala Gly Ser Lys Ile Arg Gln Tyr Arg Glu Glu Arg
 1               5                  10                  15

Thr Leu Ser Arg Ala Ala Phe Gly Ala Trp Phe Asp Thr Pro Gly Ser
                20                  25                  30

Thr Val Gln Gly Trp Glu Thr Asp Gly Lys Arg Ala Asn Thr Lys Val
            35                  40                  45

Met Asn Gln Ile Ala Ala Met Gly Ile Ala Glu His Ala Asp Trp His
        50                  55                  60

Val Ala Val Arg Asp Val Glu Ser Ala Met Ala Ser Trp Thr Pro Asp
 65                  70                  75                  80

Ser Trp Thr Arg Ala Glu Ala Arg Gln Met Pro Gln Tyr Pro Asp Lys
                85                  90                  95

Ser Ala Leu Asp Ala Ala Thr Arg Gln Leu Ser Ser Tyr Pro Pro Leu
            100                 105                 110

Val Phe Ala Gly Glu Ala Arg Glu Leu Thr Thr Glu Leu Gly Lys Val
        115                 120                 125

Ala Arg Gly Glu Ala Phe Leu Leu Gln Gly Gly Asp Cys Ala Glu Ser
    130                 135                 140

Phe Ala Glu Phe His Pro Asn Asn Ile Arg Asp Thr Phe Arg Val Ile
145                 150                 155                 160

Leu Gln Met Ala Val Val Leu Thr Phe Ala Ser Lys Leu Pro Thr Val
                165                 170                 175

```
Lys Leu Gly Arg Met Ala Gly Gln Phe Ala Lys Pro Arg Ser Ala Asp
                180                 185                 190

Thr Glu Val Ile Asp Gly Val Glu Leu Pro Ser Tyr Arg Gly Asp Asn
            195                 200                 205

Val Asn Asp Ile Ala Phe Thr Pro Glu Ala Arg Ile Pro Asp Pro Gln
    210                 215                 220

Arg Met Val Gln Gly Tyr Ser Gln Ser Ala Ala Thr Leu Asn Leu Leu
225                 230                 235                 240

Arg Ala Phe Ala Gly Gly Gly Tyr Ala Asn Leu His Gln Val His Lys
                245                 250                 255

Trp Thr Leu Asp Phe Met Gly Lys Ser Pro Trp Ser Ala Lys Phe Ala
            260                 265                 270

Asp Val Ala Asp Arg Ile Gly Glu Ala Leu Asp Phe Met Glu Ala Cys
    275                 280                 285

Gly Ile Asn Pro Asp Thr Val Pro Gln Leu Lys Gly Thr Ala Phe Tyr
290                 295                 300

Thr Ser His Glu Ala Leu Leu Leu Pro Tyr Glu Gln Ala Leu Thr Arg
305                 310                 315                 320

Gln Asp Ser Leu Thr Gly Asp Trp Tyr Asp Thr Ser Ala His Phe Leu
                325                 330                 335

Trp Ile Gly Asp Arg Thr Arg Phe Glu Gly Ser Ala His Val Glu Phe
            340                 345                 350

Leu Arg Gly Ile Gly Asn Pro Ile Gly Met Lys Cys Gly Pro Ser Leu
    355                 360                 365

Glu Pro Asp Ala Leu Leu Arg Leu Leu Asp Thr Leu Asn Pro Gly Arg
370                 375                 380

Val Pro Gly Arg Met Thr Leu Ile Thr Arg Tyr Gly His Asp Lys Ile
385                 390                 395                 400

Glu Thr Gly Leu Pro Lys Leu Val Arg Ala Val Lys Arg Glu Gly His
                405                 410                 415

Pro Val Val Trp Ser Cys Asp Pro Met His Gly Asn Val Val Lys Ala
            420                 425                 430

Ala Asn Gly Tyr Lys Thr Arg Pro Phe Asp Arg Ile Leu Ala Glu Val
    435                 440                 445

Arg Gly Phe Phe Ala Val His Arg Ala Glu Gly Thr Phe Ala Gly Gly
450                 455                 460

Ile His Ala Glu Met Thr Gly Glu Asn Val Thr Glu Cys Thr Gly Gly
465                 470                 475                 480

Ala Ile Ala Ile Thr Glu Gln Gly Leu Ala Asp Arg Tyr His Thr His
                485                 490                 495

Cys Asp Pro Arg Leu Asn Ala Gly Gln Ser Leu Glu Leu Ala Phe Leu
            500                 505                 510

Leu Ala Glu Met Leu Asn Asp Glu Met Ala Glu Arg Arg Lys Ala Ala
    515                 520                 525

Ala

<210> SEQ ID NO 9
<211> LENGTH: 183
<212> TYPE: DNA
<213> ORGANISM: Sphingomonas sp.

<400> SEQUENCE: 9
atgatcgcaa acgggtgcg gaccgagaat ttctcctcgc gcgcgcgatc ccagccctcg      60
accaccgggg gctgcggcgt gggcagcggg gtcttgggaa aggcgatcgg cgtcgcgacc    120
```

| | |
|---|---:|
| ggtccggcca cggcggtcgt caggtcggca tcggtcagcg gcgtgacgaa ttcgcagcca | 180 |
| tag | 183 |

<210> SEQ ID NO 10
<211> LENGTH: 105
<212> TYPE: DNA
<213> ORGANISM: Sphingomonas sp.

<400> SEQUENCE: 10

| | |
|---|---:|
| atgcccggcg gcgcgttgct cagcggagca gcgcgcccgc cagcgcccac aggccatagc | 60 |
| cgagcacgaa caccagcatt caggcgatca ccgcgctgcc ggtga | 105 |

<210> SEQ ID NO 11
<211> LENGTH: 1587
<212> TYPE: DNA
<213> ORGANISM: Sphingomonas sp.

<400> SEQUENCE: 11

| | |
|---|---:|
| atgacgacgt tagccggttc caagatccgc cagtatcgcg aagaacgcac cctcagccgc | 60 |
| gccgccttcg gtgcctggtt cgacacgcca ggctctaccg tgcagggctg ggagaccgac | 120 |
| ggcaagcgcg ccaataccaa ggtgatgaac cagattgcgg cgatgggaat cgccgagcat | 180 |
| gcggactggc acgtcgccgt ccgcgacgtg gagagtgcaa tggcaagctg gaccccgat | 240 |
| agctggacgc gcgccgaagc gcgccagatg ccacaatatc cggacaagag cgcgctcgac | 300 |
| gccgccaccc ggcagctgag cagctatccg ccgctggtct cgccggaga gcgcgcgag | 360 |
| ctcaccaccg agctgggcaa ggtcgcgcgc ggcgaggcct cctgctcca gggcggcgac | 420 |
| tgcgccgaga gcttcgccga gttccatccg aacaacatcc gcgacacctt ccgcgtgatc | 480 |
| ctgcagatgg cggtggtcct caccttcgcc tcgaagctgc cgacggtgaa gctcggacgg | 540 |
| atggccggcc agttcgccaa gccgcgctcg gccgataccg aggtgatcga cggtgtcgag | 600 |
| ctgcccagct accgcggcga taacgtcaac gacatcgcct tcacgcccga ggcgcggatc | 660 |
| cccgatccgc agcggatggt gcagggctac agccagtcgg cggcgacgct caatctgctg | 720 |
| cgcgcctttg cgggtggcgg ctatgcgaac ctgcatcagg tgcacaagtg gacgcttgat | 780 |
| ttcatgggca agagccctg gtcggccaag ttcgccgatg tcgccgaccg gatcggcgag | 840 |
| gcgctcgact tcatggaggc gtgcgggatc aaccccgata ccgtgccgca actgaagggc | 900 |
| accgacttct acaccagcca cgaggcgctt ctgctcccct atgagcaggc gctgacccgg | 960 |
| caggacagcc tgaccggcga ctggtacgat acctcggcgc acttcctgtg gatcggcgac | 1020 |
| cgcacccgct tcgagggctc ggcgcatgtc gagttcctgc gcggcatcgg caatccgatc | 1080 |
| gggatgaagt gcgggccgag cctcgagccc gacgcgctgc tgcggctgct cgacacgctc | 1140 |
| aacccgggcc gcgtgcccgg ccgcatgacg ctgatcacgc gctatggcca cgacaagatc | 1200 |
| gagacgggcc tgcccaagct ggtccgcgcg gtgaagcgcg agggccatcc ggtggtgtgg | 1260 |
| agctgcgatc cgatgcacgg caacgtcgtc aaggccgcga acggctacaa gacgcggccg | 1320 |
| ttcgaccgga tccttgccga ggtgcgcggc ttcttcgccg tccaccgcgc cgagggcacc | 1380 |
| ttcgccggcg gcatccatgc cgagatgacc ggtcagaatg tgaccgagtg caccggcggc | 1440 |
| gcgatcgcga tcaccgagca gggcctggcc gatcgctacc acacgcattg cgacccgcgg | 1500 |
| ctcaacgcgg gtcagagcct ggagctggcc ttcctactcg ccgagatgct caacgacgaa | 1560 |
| atggcggagc gtcgcaaggc cgccgcc | 1587 |